US012311048B2

(12) United States Patent
Mitragotri et al.

(10) Patent No.: US 12,311,048 B2
(45) Date of Patent: May 27, 2025

(54) CROSSLINKED MATERIALS

(71) Applicant: Fount Bio, Inc., Cambridge, MA (US)

(72) Inventors: Samir Mitragotri, Lexington, MA (US); Eric Spengler, Cambridge, MA (US); Douglas Levinson, Sherborn, MA (US); Douglas R. Vogus, Cambridge, MA (US)

(73) Assignee: Fount Bio, Inc., Cambridge, MA (US)

( * ) Notice: Subject to any disclaimer, the term of this patent is extended or adjusted under 35 U.S.C. 154(b) by 651 days.

(21) Appl. No.: 17/289,468

(22) PCT Filed: Nov. 1, 2019

(86) PCT No.: PCT/US2019/059553
§ 371 (c)(1),
(2) Date: Apr. 28, 2021

(87) PCT Pub. No.: WO2020/093022
PCT Pub. Date: May 7, 2020

(65) Prior Publication Data
US 2023/0165780 A1 Jun. 1, 2023

Related U.S. Application Data

(60) Provisional application No. 62/754,995, filed on Nov. 2, 2018.

(51) Int. Cl.
| | | |
|---|---|---|
| *A61K 8/73* | (2006.01) |
| *A61K 8/44* | (2006.01) |
| *A61K 8/49* | (2006.01) |
| *A61K 8/81* | (2006.01) |
| *A61K 8/86* | (2006.01) |
| *A61Q 19/00* | (2006.01) |
| *C08J 3/24* | (2006.01) |

(52) U.S. Cl.
CPC .............. *A61K 8/735* (2013.01); *A61K 8/44* (2013.01); *A61K 8/49* (2013.01); *A61K 8/8147* (2013.01); *A61K 8/86* (2013.01); *A61Q 19/00* (2013.01); *C08J 3/24* (2013.01); *A61K 2800/87* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 8,038,991 B1 * | 10/2011 | Stankus | A61K 38/40 |
| | | | 424/530 |
| 9,932,333 B2 | 4/2018 | Kanai et al. | |
| 10,624,865 B2 | 4/2020 | Pathak | |
| 2004/0127699 A1 | 7/2004 | Zhao et al. | |
| 2006/0008428 A1 | 1/2006 | Seyler et al. | |
| 2006/0159714 A1 | 7/2006 | Thorel | |
| 2007/0142575 A1 * | 6/2007 | Zheng | A61K 8/895 |
| | | | 428/447 |
| 2009/0156480 A1 | 6/2009 | Akashi et al. | |
| 2011/0223625 A1 | 9/2011 | Kelts et al. | |
| 2013/0096081 A1 | 4/2013 | Njikang et al. | |
| 2013/0165463 A1 * | 6/2013 | Gurtner | A61K 45/06 |
| | | | 514/275 |
| 2014/0227174 A1 | 8/2014 | Muraski et al. | |
| 2014/0256831 A1 | 9/2014 | Ito et al. | |
| 2017/0348218 A1 | 12/2017 | Chen et al. | |
| 2018/0186900 A1 | 7/2018 | Mitragotri et al. | |
| 2022/0175819 A1 | 6/2022 | Mitragotri et al. | |

FOREIGN PATENT DOCUMENTS

| | | |
|---|---|---|
| CA | 3118491 A1 | 5/2020 |
| CN | 103097388 A | 5/2013 |
| CN | 105407920 A | 3/2016 |
| CN | 113365602 A | 9/2021 |
| JP | 2009-519239 A | 5/2009 |
| JP | 2016-106112 A | 6/2016 |
| WO | WO-2007/064773 A2 | 6/2007 |
| WO | WO-2008/016983 A2 | 2/2008 |
| WO | WO-2009/108100 A1 | 9/2009 |
| WO | WO-2012/010704 A1 | 1/2012 |
| WO | WO-2013/159064 A1 | 10/2013 |
| WO | WO-2014/057139 A2 | 4/2014 |
| WO | WO-2014/178878 A1 | 11/2014 |
| WO | WO-2016/010092 A1 | 1/2016 |
| WO | WO-2016/201382 A1 | 12/2016 |
| WO | WO-2017/173026 A1 | 10/2017 |
| WO | WO-2020/093022 A1 | 5/2020 |
| WO | WO-2020/214889 A1 | 10/2020 |
| WO | WO-2022/094002 A1 | 5/2022 |

OTHER PUBLICATIONS

International Search Report for PCT/US2021/056916, 5 pages (Feb. 8, 2022).
Written Opinion for PCT/US2021/056916, 9 pages (Feb. 8, 2022).
Bos, J. D. and Meinardi, M. M., The 500 Dalton rule for the skin penetration of chemical compounds and drugs, Experimental Dermatology, 9(3):165-169 (2000).
Doyle, G. and Mccutcheon, J., Development of an Open Source Educational Resource: "Clinical Procedures for Safer Patient Care", Stud. Health Technol. Inform., 225:979-980 (2016).
Jinglong Cai et al., Scar Plastic and Aesthetic Surgery, Zhejiang Science and Technology Press, pp. 534-536 (2015).
Mcconville, A., et al., Mini-Review: Assessing the Potential Impact of Microneedle Technologies on Home Healthcare Applications, Medicines (Basel), 5(2):50 (2018).
Ruan, S., Ligand-Mediated and Enzyme-Directed Precise Targeting and Retention for the Enhanced Treatment of Glioblastoma, ACS Applied Materials& Inferfaces vol. 9, No. 24 (2017).

(Continued)

*Primary Examiner* — Jennifer A Berrios
(74) *Attorney, Agent, or Firm* — Choate, Hall & Stewart LLP; Brenda H. Jarrell; Lauren E. Markham

(57) ABSTRACT

The present application describes to the synthesis, formulation and uses of crosslinkable entities and crosslinked materials.

13 Claims, 18 Drawing Sheets

(56) References Cited

OTHER PUBLICATIONS

Ruel-Gariepy, E. and Leroux, J-C., In situ-forming hydrogels—review of temperature-sensitive systems, Eur J Pharm Biopharm, 58(2):409-26 (2004).

Seal, B. L., et al., Polymeric biomaterials for tissue and organ regeneration, Materials Science and Engineering, 34(4-5):147-230 (2001).

Srinivas, P. et al., Micro Needle Patches in Drug Delivery—A Review, International Journal of Pharmacy and Technology, 2(3):329-344 (2010).

Wang, Z. et al., Supplementary Material for Hierarchical Assembly of Bioactive Amphiphilic Molecule Pairs into Supramolecular Nanofibril Self-Supportive Scaffolds for Stem Cell Differentiation, XP055706252 (2016).

Dubikovskaya, E. et al., Precursor molecules for the synthesis of D-luciferin, WO2014057139A2, pp. 1-2 (2014).

International Search Report for PCT/US20/28639 (Delivery and Retention of Active Agents Within the Skin, filed Apr. 17, 2020), received by ISA/EP, 7 pages (Jul. 1, 2020).

International Search Report for PCT/US2019/059553 (Crosslinked Materials, filed Nov. 1, 2019), received from ISA/EP, 5 pages (Feb. 21, 2020).

Ng, K.W. and Lau, W.M., Skin Deep: The Basics of Human Skin Structure and Drug Penetration, N. Dragicevic, H.I. Maibach (eds.), *Percutaneous Penetration Enhancers Chemical Methods in Penetration Enhancement: Drug Manipulation Strategies and Vehichle Effects*, Springer-Verlag Berlin Heidelberg, 9 pages (2015).

Ruan, S. et al., Ligand-Mediated and Enzyme-Directed Precise Targeting and Retention for the Enhanced Treatement of Glioblastoma, ACS Appl. Mater. Interfaces., 9:20348-20360 (2017).

Wang, P. et al., Site-specific immobilization of biomolecules by a biocompatable reaction between terminal cysteine and 2-cyanobenzothiazole, Chem. Commun., 49:8644-8646 (2013).

Wang, Z. et al., Hierarchical Assembly of Bioactive Amphiphilic Molecule Pairs into Supramolecular Nanofibril Self-Supportive Scaffolds for Stem Cell Differentiation, J. Am. Chem. Soc., 138:15027-15034 (2016).

Written Opinion for PCT/US20/28639 (Delivery and Retention of Active Agents Within the Skin, filed Apr. 17, 2020), received by ISA/EP, 10 pages (Jul. 1, 2020).

Written Opinion for PCT/US2019/059553 (Crosslinked Materials, filed Nov. 1, 2019), received from ISA/EP, 9 pages (Feb. 21, 2020).

Yuan, Y. et al., Intracellular Self-Assembly of Taxol Nanoparticles for Overcoming Multidrug Resistance, Angew. Chem. Int. Ed., 54:9700-9704 (215).

Zhang, X. et al., Improved method for synthesis of cysteine modified hyaluronic acid for in situ hydrogel formation, Chemical Communications, 51:9662-9665 (2015).

Casale, J. and Crane, J.S., Biochemistry, Glycosaminoglycans. [Updated Mar. 27, 2023]. In: StatPearls [Internet]. Treasure Island (FL): StatPearls Publishing; Jan. 2024-. Available from: https://www.ncbi.nlm.nih.gov/books/NBK544295/.

* cited by examiner

CROSSLINKED MATERIALS

BACKGROUND

Various systems have been developed for the installation or generation of crosslinked materials at or on a particular site of interest, for example at a site of surgical or traumatic disruption (e.g., of organs, connective tissues, muscles, tendons and/or membranes; see, for example, Seal et al. *Mater Sci. Eng* 34:147, 2001). Some such materials have shown promise, for example, in effectively sealing internal wounds and/or achieving tissue approximation for improved wound healing (see, for example, Ruel-Gariepy et al. *Eur. J. Pharm. Biopharm.* 58:409, 2004).

SUMMARY

The present disclosure provides a variety of insights relating to provision of crosslinked materials (e.g., gels or other high molecular weight materials) in or on a target site of interest (e.g., in situ).

Among other things, the present disclosure provides an insight that lipophilicity of a crosslinkable entity (e.g., comprising a polymer moiety and a crosslink moiety) can be tuned to achieve a desired rate and/or extent of penetration after application to a site (e.g., on a skin surface or otherwise to a skin site above a target site of interest).

Alternatively or additionally, the present disclosure provides an insight that low viscosity preparations of crosslinkable entities have desirable characteristics for certain embodiments, e.g., permitting the crosslinked material(s) they generate to better fill spaces and/or structures (e.g., microcavities on surfaces) therein, and/or to make better contacts with tissues and/or structures thereon.

Alternatively or additionally, the present disclosure provides an insight that a crosslinked material as provided by the present disclosure may exhibit improved durability/persistence relative to its initial crosslinkable entities (e.g., separate from one another and/or prior to their crosslinking to generate the relevant crosslinked material) in a relevant biological system.

Still further, the present disclosure provides an insight that ensuring first and second crosslinkable entities are separate (i.e., chemically, physically, and/or spatially) on administration (e.g., while being administered), can be beneficial and/or otherwise desirable in certain embodiments.

Among other things, the present disclosure provides embodiments in which one or more of a set of crosslinkable entities that, by crosslinking with one another generate a crosslinked material, is characterized by a degree of lipophilicity as described herein. The present disclosure also provides embodiments in which one or more crosslinkable entities is utilized as a low viscosity preparation. The present disclosure also provides embodiments in which individual crosslinkable entities are maintained separate from one another upon administration (e.g., up to and/or during administration). The present disclosure further provides combinations of such embodiments, as well as insights with respect to particular context(s) in which one or more such embodiments might be particularly useful or effective.

Among other things, provided insights permit selection and/or utilization of crosslinkable entities or components (e.g., polymer and/or crosslink moieties) or combinations thereof not previously contemplated or utilized for in situ crosslinking systems, and/or provide new methodologies for administration of crosslinkable entities to achieve an in situ crosslinked material.

In some embodiments, the present disclosure provides systems comprising components that together can be used to provide in situ crosslinked materials. In some embodiments, provided systems comprise first and second crosslinkable entities, at least one (and, in many embodiments, both) of which has lipophilicity as described herein, which first and second entities crosslink with one another to form a crosslinked material (e.g., a gel) with material and/or functional characteristics as described herein at or on a site of interest (e.g., in situ).

In some embodiments, the present disclosure provides methods of making and/or using such provided systems, and/or components thereof.

In some provided methods, first and second crosslinkable entities are separately and serially administered to a site (e.g., on a skin surface); in some such embodiments, the first crosslinkable entity is first administered, and the second crosslinkable entity is administered after a period of time.

Also provided are various devices and technologies for storing and/or administering first and/or second crosslinkable entities. In some embodiments, provided devices maintain the first and second crosslinkable entities in physically separate locations, compartments, and/or containers.

BRIEF DESCRIPTION OF THE DRAWING

FIG. 9B is an image of the crosslinked HA-gly-CBT gel after a 24-h incubation with hyaluronidase.

FIG. 11A shows a comparison of GPC signal from HA-gly-CBT to GPC signals measured for stratum corneum (SC) extracts and epidermis/dermis extracts, averaged over six samples. FIG. 11B illustrates average GPC signal for SC extracts with associated error bars.

FIG. 11C illustrates average GPC signal for epidermis/dermis extracts with associated error bars.

FIG. 18A presents fluorescent, microscopy images of skin samples obtained with a Cy5 filter. FIG. 18B presents quantitive data of HA-gly-CBT to the SC, epidermis, and dermis.

DEFINITIONS

Figure 1:
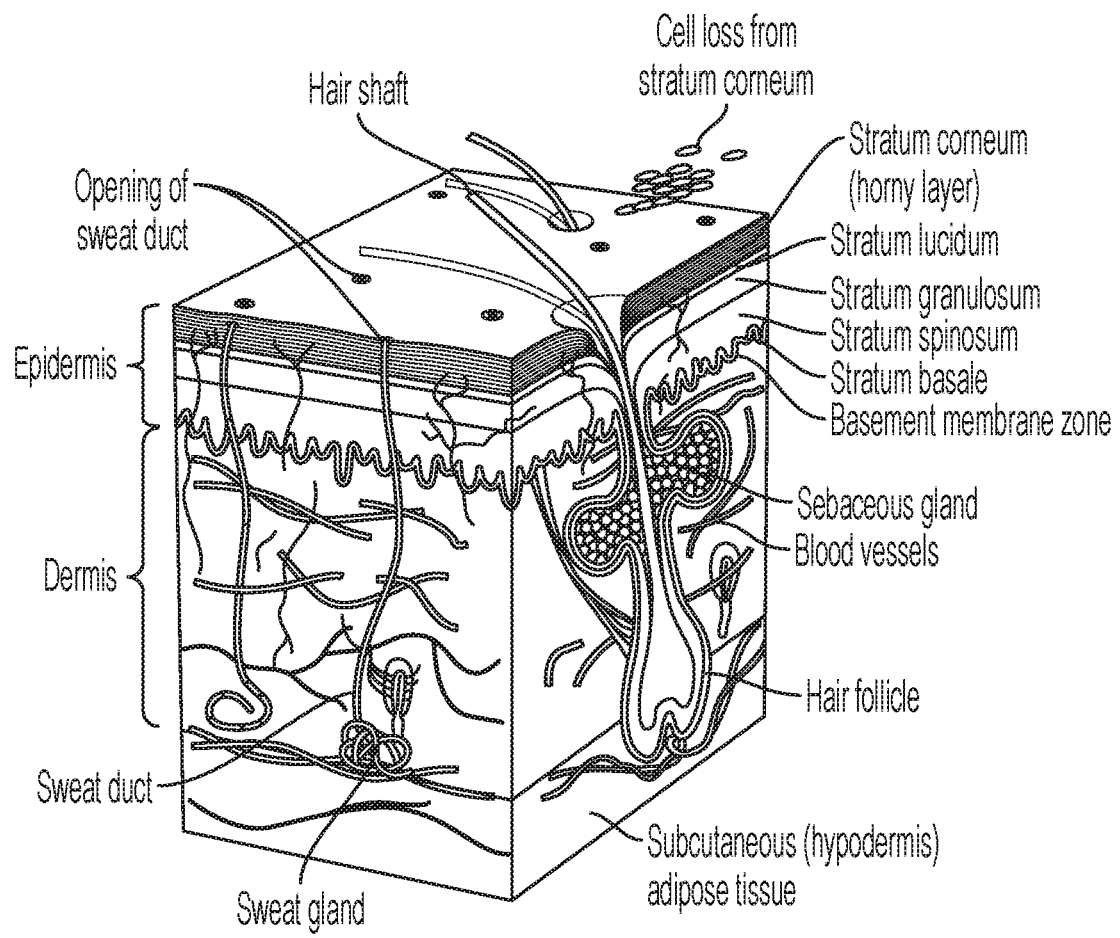
FIG. 1 illustrates parts of human skin including epidermis and dermis.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Associated: Two events or entities are "associated" with one another, as that term is used herein, if the presence, level and/or form of one is correlated with that of the other. For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Biocompatible: The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

Comparable: As used herein, the term "comparable" refers to two or more agents, entities, situations, sets of conditions, etc., that may not be identical to one another but that are sufficiently similar to permit comparison therebetween so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Corresponding to: As used herein in the context of polypeptides, nucleic acids, and chemical compounds, the term "corresponding to", designates the position/identity of a structural element, e.g., of an amino acid residue, a nucleotide residue, or a chemical moiety, in a compound or composition through comparison with an appropriate reference compound or composition. For example, in some embodiments, a monomeric residue in a polymer (e.g., an amino acid residue in a polypeptide or a nucleic acid residue in a polynucleotide) may be identified as "corresponding to" a residue in an appropriate reference polymer. For example, those of ordinary skill will appreciate that, for purposes of simplicity, residues in a polymer may be designated using a canonical numbering system based on a reference related polymer, so that a residue "corresponding to" one at position 190 of a reference polymer, for example, need not actually be the $190^{th}$ residue in a polymer of interest, but rather refers to the residue that corresponds to the residue found at position 190 in the reference polymer; those of ordinary skill in the art readily appreciate how to identify "corresponding" residues in polymers (e.g., using commercially available sequence comparison software for polypeptide and nucleic acid polymers; optionally manually for other polymers).

Designed: As used herein, the term "designed" refers to an agent (i) whose structure is or was selected by the hand of man; (ii) that is produced by a process requiring the hand of man; and/or (iii) that is distinct from natural substances and other known agents.

Dosage form: Those skilled in the art will appreciate that the term "dosage form" may be used to refer to a physically discrete unit of an agent (e.g., a therapeutic, diagnostic or cosmetic agent) for administration to a subject. Typically, each such unit contains a predetermined quantity of agent. In some embodiments, such quantity is a unit dosage amount (or a whole fraction thereof) appropriate for administration in accordance with a dosing regimen that has been determined to correlate with a desired or beneficial (e.g., therapeutic and/or cosmetic) outcome when administered to a relevant population (i.e., with a therapeutic dosing regimen). In some embodiments, such quantity is a unit dosage amount (or a whole fraction thereof) appropriate for administration in accordance with a regimen that has been determined to correlate with a desired or beneficial cosmetic outcome (e.g., provides visible and/or tactile improvement to skin) when administered to a relevant population. Those of ordinary skill in the art appreciate that the total amount of a composition or agent administered to a particular subject is determined by one or more attending professionals (e.g., physicians, nurses, or other licensed professionals) and may involve administration of multiple dosage forms. In some embodiments, a dosage form may be provided in a formulation that is or comprises a cream, gel, liquid, lotion, mist, mask, matrix, particle, paste, patch, powder, serum, solid, spray (or collection thereof), or a combination thereof.

Dosing regimen: Those skilled in the art will appreciate that the term "dosing regimen" may be used to refer to a set of unit doses (typically more than one) that are administered individually to a subject, typically separated by periods of time. In some embodiments, a given agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population.

Excipient: as used herein, refers to an inactive (e.g., not a therapeutic active such as a cosmetic active) agent that may be included in a pharmaceutical composition, for example to provide or contribute to a desired consistency or stabilizing effect.

"Improve," "increase", "inhibit" or "reduce": As used herein, the terms "improve", "increase", "inhibit', "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

In Situ: as used herein, the term "in situ" refers to a location at, in, or on a target site. For example, in some embodiments, crosslinkable entities crosslink in situ when they react to form a crosslinked material at, in, or on a target site of interest, for example, on a tissue surface or within a tissue; in many embodiments, a relevant tissue is skin.

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients.

Linker: as used herein, is used to refer to that portion of a multi-element agent that connects different elements to one another.

Marker: A marker, as used herein, refers to an entity or moiety whose presence or level is a characteristic of a particular state or event. In some embodiments, presence or level of a particular marker may be characteristic of presence, state, or stage of a disease, disorder, or condition.

Subject: As used herein, the term "Subject" refers to any organism to which a provided system is or may be administered, e.g., for experimental, diagnostic, prophylactic, cosmetic, and/or therapeutic purposes. Typical subjects include animals (e.g., mammals such as mice, rats, rabbits, non-human primates, and/or humans). In some embodiments, a subject is a human. In some embodiments, a subject is suffering from or susceptible to one or more disorders or conditions. In some embodiments, a subject displays one or more symptoms of a disorder or condition. In some embodiments, a subject has been diagnosed with one or more disorders or conditions. In some embodiments, the disorder or condition is or includes cancer, or presence of one or more tumors. In some embodiments, the subject is receiving or has received certain therapy to diagnose and/or to treat a disease, disorder, or condition. In some embodiments, a subject refers to a human seeking cosmetic benefit and/or improvement, such as an improvement of appearance and/or feel of skin.

Physiological conditions: As used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a target site of interest. Physiological conditions typically include one or more of, e.g., a temperature within the range of 20-40° C. (and specifically about 37° C.), atmospheric pressure of 1, pH of 6-8, glucose concentration of 1-20 mM, oxygen concentration at atmospheric levels, and gravity as it is encountered on earth.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Sample: As used herein, the term "sample" typically refers to an aliquot of material obtained or derived from a source of interest. In some embodiments, a source of interest is a biological or environmental source. In some embodiments, a source of interest may be or comprise a cell or an organism, such as a microbe, a plant, or an animal (e.g., a human). In some embodiments, a source of interest is or comprises biological tissue or fluid. In some embodiments, a sample is a "primary sample" obtained directly from a source of interest by any appropriate means. In some embodiments, as will be clear from context, the term "sample" refers to a preparation that is obtained by processing (e.g., by removing one or more components of and/or by adding one or more agents to) a primary sample. Such a "processed sample" may comprise, for example, materials extracted from a sample or obtained by subjecting a primary sample to one or more techniques such as chromatography, extraction, precipitation, etc.

Substantial structural similarity: As used herein, the term "substantial structural similarity" refers to presence of shared structural features at particular positions. In some embodiments, the term "substantial structural similarity" refers to presence and/or identity of structural elements such as, for example: loops, sheets, helices, H-bond donors, H-bond acceptors, glycosylation patterns, salt bridges, disulfide bonds, and combinations thereof. In some embodiments, the term "substantial structural similarity" refers to three dimensional arrangement and/or orientation of atoms or moieties relative to one another (for example: distance and/or angles between or among them between an agent of interest and a reference agent).

Therapeutic agent: As used herein, the phrase "therapeutic agent" in general refers to any agent that elicits a desired pharmacological effect (which may, in some embodiments, be or comprise a cosmetic effect) when administered to an organism. In some embodiments, an agent is considered to exhibit an effect (i.e., to be a therapeutic agent) if it demonstrates a statistically significant effect across an appropriate population. In some embodiments, the appropriate population may be a population of model organisms. In some embodiments, an appropriate population may be defined by particular criteria, such as a certain age group, gender, genetic background, preexisting clinical conditions, etc, or combinations thereof. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a therapeutic agent is one that achieves a cosmetic effect (i.e., is a cosmetic agent). In some embodiments, a therapeutic agent can be used to achieve improvement of appearance and/or feel of skin, and/or another cosmetic benefit.

Treat: As used herein, the term "treat," "treatment," or "treating" refers to partial or complete alleviation, amelioration, delay of onset of, inhibition, prevention, relief, and/or reduction in incidence and/or severity of one or more symptoms or features of a disease, disorder, and/or condition, or achievement of another desired physiological effect (e.g., a desired cosmetic effect such as improvement of appearance and/or feel of skin, such as visible and/or tactile improvement to skin. In some embodiments, treatment comprises administration of an agent which results in a physiological effect. In some embodiments treatment comprises a cosmetic treatment which upon administration improves physical appearance in manner described herein. In some embodiments, treatment may be administered to a subject who does not exhibit signs or features of a disease, disorder, and/or condition (e.g., may be prophylactic). In some embodiments, treatment may be administered to a subject who exhibits only early or mild signs or features of the disease, disorder, and/or condition, for example for the purpose of decreasing the risk of developing pathology associated with the disease, disorder, and/or condition. In some embodiments, treatment may be administered to a subject who exhibits established, severe, and/or late-stage signs of the disease, disorder, or condition.

DETAILED DESCRIPTION OF CERTAIN EMBODIMENTS

Crosslinkable Entities

The present disclosure provides certain technologies relating to administration of crosslinkable entities to a subject, and particular to in situ crosslinking of such crosslinkable entities at, in, or on a target site which, for example, may be a site in or on skin, for example on, at, in, or below the epidermis, dermis or underlying hypodermis.

In some embodiments, the present disclosure provides technologies for administering a system that comprises first and second crosslinkable entities, selected and/or designed to achieve formation of an in situ crosslinked material. Those skilled in the art, reading the present disclosure, will appreciate that such crosslinked material will typically be characterized by one or more different physical properties, such as rheology, and/or chemical properties, such as molecular weight, relative to its parent cross-linkable entities. In some embodiments, such different property(ies) may be or include improved durability/persistence, e.g., in situ and/or otherwise in a relevant biological system.

As described herein, such first and second crosslinkable entities are characterized by an ability, when contacted with one another, to react with one another to form the crosslinked material in situ, e.g., absent administration of a catalyst or other non-participating agent.

In many embodiments, at least one of the crosslinkable entities will comprise a polymer moiety linked with a crosslink moiety. In some embodiments, at least one of the crosslinkable entities will not comprise a polymer moiety. In some embodiments, a pair of crosslinkable entities that react with one another (e.g., absent administration of a catalyst or other non-participating agent) each comprise a polymer moiety linked with a crosslink moiety. In some embodiments, a pair crosslinkable entities that react with one another (e.g., absent administration of a catalyst or other non-participating agent) comprises a first crosslinkable entity that comprises a polymer moiety linked with a crosslink moiety and a second crosslinkable entity that does not comprise a polymer moiety.

In some embodiments, a crosslinkable entity comprises a polymer moiety and a plurality of crosslink moieties, which may be the same or different. Among other things, the present disclosure provides insights and technologies relevant to achieving penetration of crosslinkable entities to a target site in skin (e.g., on, at, in, or below the epidermis, dermis or underlying hypodermis). For example, in some embodiments, the present disclosure teaches that lipophilicity within a particular range may permit desirable (e.g., enhanced) penetration of a crosslinkable entity, and particularly of a crosslinkable entity comprising a polymer moiety and a crosslinkable moiety.

As shown in FIG. 1, human skin is multi-layered, comprising an external epidermis (which itself is a layered structure comprising the stratum corneum, stratum lucidum, stratum granulosum, stratum spinosum, and stratum basale), a dermis, and an underlying hypodermis. The skin acts as a barrier to separate and protect the body from its environment. A major challenge in the cosmetic and dermatological fields is the development of technologies to facilitate penetration of compounds or agents of interest across skin. See, for example, Ng (2015) Skin Deep: The Basics of Human Skin Structure and Drug Penetration. In: Dragicevic N., Maibach H. (eds) Percutaneous Penetration Enhancers Chemical Methods in Penetration Enhancement. Springer, Berlin, Heidelberg It is understood in the art that human skin restricts transport of compounds with a molecular weight (e.g., a number average molecular weight) above about 500 Daltons (Bos and Meinardi, *Experimental Dermatology*, 9:165, 2000), and even for such small compounds, effective transport often requires additional manipulation, such as administration of a chemical or physical abrading or disrupting agent and/or of electrical current or magnetic field, etc.

The present disclosure, among other things, provides technologies relating to penetration across or through skin layer(s) and specifically relates to such penetration by crosslinkable entities that react to generate a crosslinked material that is present at a target site. In many embodiments, the target site may be on, at, in or below the epidermis, dermis or underlying hypodermis. Among other things, the present disclosure provides a teaching that crosslinkable entities with improved skin penetration characteristic(s) can be designed and/or prepared by modulating lipophilicity. For example, in some embodiments, the present disclosure teaches that rate and/or extent of skin penetration by a particular agent (and specifically by an agent that is or comprises a polymer moiety and/or otherwise has a number molecular weight (e.g., a number average molecular weight) above 500 daltons, and even within a range of 10-500 kDa) can be enhanced by increasing lipophilicity of the agent, for example by attaching one or more hydrophobic moieties to the agent. Those of ordinary skill in the art will appreciate that, in some embodiments, hydrophobic moieties that increase lipophilicity may be or comprise crosslink moieties; alternatively or additionally, in some embodiments, such hydrophobic moieties may not necessarily be or comprise crosslink moieites and/or may not necessarily participate in crosslinks (e.g., that are in and/or that help generate a crosslinked material as described herein)

Alternatively or additionally, in some embodiments, the present disclosure provides technologies relating to providing a crosslinked material in a target site in or on a tissue (and particularly in or on skin), so that contacts between the material and surfaces of the target site are maximized. In some embodiments, such surfaces may include one or more cavities or irregularities, which may, in some embodiments, be micro- or even nano-scale structures. In some embodiments, the present disclosure provides preparations of crosslinkable moieties that have flow characteristics that facilitate such contacts.

In some particular embodiments, a crosslinkable entity for use in accordance with the present disclosure comprises a polymer moiety linked with a crosslink moiety, where the crosslink moiety imparts increased lipophilicity to the conjugate (i.e., to the crosslinkable entity) as compared with the polymer moiety alone; as described herein, in some embodiments, such a crosslink moiety can also improve skin penetration by the crosslinkable entity as compared with that of the polymer moiety alone.

In some embodiments, depth of penetration of a crosslinkable entity will be assessed and/or described in terms of the absolute distance (e.g., in microns) below the surface of the skin. In some embodiments, depth of penetration of a crosslinkable entity will be assessed and/or described in terms of number of cells below the surface of the skin.

In some embodiments, a crosslinkable entity as described herein can and/or does (e.g., when administered as described herein) penetrate to a specified depth into the skin, for example within a particular time period. In some embodiments, a such a specified depth may be, for example, at least 50 microns, at least 100 microns, at least 200 microns, or more; alternatively or additionally, in some embodiments, such specified depth may be at least 2 cell layers, at least 3 cell layers, at least 4 cell layers, at least 5 cell layers, at least 6 cell layers, at least 7 cell layers, at least 8 cell layers, at least 9 cell layers, at least 10 cell layers or more, and/or such time period may be, for example, within 1 day, within 18 hours, within 12 hours, within 11 hours, within 10 hours, within 9 hours, within 8 hours, within 7 hours, within 6 hours, within 5 hours, within 4 hours, within 3 hours, within 2 hours, within 1 hour or less.

In some embodiments, at least 1% of a crosslinkable entity administered to a skin surface penetrates to a target site on, at, in, or below the epidermis, dermis or underlying hypodermis, for example within a time period of 1 day. In some embodiments, skin penetration characteristic(s) of a crosslinkable entity as described herein are observed in the absence of any chemical or physical abrading or disrupting agent and/or of electrical current or magnetic field, etc (e.g., absent a penetration enhancer as understood in the art).

In some embodiments, a crosslinkable entity is characterized by lipophilicity (log P) within a range of about −4 and about 2. In some embodiments, crosslinkable entities described herein comprise a crosslinkable moiety, which is lipophilic. In some embodiments, lipophilicity of a crosslinkable moiety may be determined independently from that of a polymer moiety, and/or of a crosslinkable entity comprising the polymer moiety and one or more crosslinkable moieties. In some embodiments, a crosslinkable moiety is characterized by lipophilicity (log P) within a range of about 0 and about 6. For example, in some embodiments, lipophilicity of a crosslinkable moiety is tested through examination of the crosslinkable moiety prior to association and/or linking with molecule polymer moiety to form a crosslinkable entity.

In some embodiments, lipophilicity for a particular entity or moiety is determined by its partition co-efficient (P) relative to a standard solvent (e.g. octanol) and water or solution thereof:

$$\log P = \log \frac{[\text{Entity or Moiety being assessed in Octanol}]}{[\text{Crosslinkable Entity or Moiety being assessed in } PBS]}$$

In some embodiments, log P of an entity or moiety (e.g., of a crosslinkable entity and/or of a crosslink moiety or other hydrophobic moiety) useful in accordance with the present disclosure is greater than 0.

In some embodiments, a crosslinkable entity (e.g., a crosslinkable entity with a lipophilicity as described herein) has a molecular weight (e.g., a number average molecular weight) above 500 daltons. In some embodiments, a crosslinkable entity has a molecular weight (e.g., a number average molecular weight) within a range of 1-1000 kDa. In some embodiments, a system comprises a crosslinkable entity that is about 10-250 kDa. In some embodiments, a system comprises a crosslinkable entity that has a molecular weight (e.g., a number average molecular weight) within a range of about 10-150 kDa. In some embodiments, a system comprises a crosslinkable entity that has a molecular weight (e.g., a number average molecular weight) within a range of about 10-100 kDa. In some embodiments, a system comprises a crosslinkable entity that has a molecular weight (e.g., a number average molecular weight) within a range of about 10-40 kDa. In some embodiments, a system comprises a crosslinkable entity that has a molecular (e.g., a number average molecular weight) weight of about 10 kDa. In some embodiments, a system comprises a crosslinkable entity that has a molecular weight (e.g., a number average molecular weight) of about 20 kDa. In some embodiments, a system comprises a crosslinkable entity that has a molecular weight (e.g., a number average molecular weight) of about 30 kDa. In some embodiments, a system comprises a crosslinkable entity that has a molecular weight (e.g., a number average molecular weight) of about 40 kDa. In some embodiments, a system comprises a crosslinkable entity that has a molecular weight (e.g., a number average molecular weight) of about 50 kDa. In some embodiments, a system comprises a crosslinkable entity that has a molecular weight (e.g., a number average molecular weight) of less than 10 kDa. In some embodiments, a system comprises a crosslinkable entity that has a molecular weight (e.g., a number average molecular weight) of less than 100 kDa. In some embodiments, a system comprises a crosslinkable entity that has a molecular weight (e.g., a number average molecular weight) of less than 250 kDa. In some embodiments, a system comprises a crosslinkable entity that has a molecular weight (e.g., a number average molecular weight) of less than 500 kDa.

In some embodiments of a crosslinkable entity that comprises a polymer moiety and a crosslink moiety, the crosslink moiety contributes lipophilicity to the crosslinkable entity. In some embodiments, the identity and/or number and/or density of crosslink moieties linked to a particular polymer moiety in a crosslinkable entity is/are selected so that the crosslinkable moiety has characteristic(s) as described herein. For example, in some embodiments, a more lipophilic crosslink moiety (and/or a larger number/higher density of lipophilic crosslink moieties) will be linked to a polymer moiety when the polymer moiety is particularly hydrophilic, particularly long, and/or is characterized by particularly poor skin penetration in its unlinked state.

Without wishing to be bound by any particular theory, we propose that, in some embodiments, it may be desirable to select a particular combination of polymer moiety and crosslink moiety (and/or number and/or density thereof) so as to achieve three-dimensional packing of the crosslinkable entity within a certain volume, e.g., which may facilitate transfer through one or more skin structures or layers (e.g., rendering the crosslinkable entity sufficiently "slippery" to pass through). In some embodiments, intra- and/or intermolecular interactions may contribute to three-dimensional packing of a crosslinkable entity. In some embodiments, three-dimensional packing of a particular cross-linkable entity as described herein occurs by self-assembly (e.g., without requiring addition of another agent), at least under certain environmental conditions (e.g., physiological conditions).

Typically, a crosslinkable entity is biocompatible. For example, in some embodiments, administration of a crosslinkable entity as described herein does not cause significant irritation and/or inflammation (e.g., at the site of administration and/or at the target site).

In some embodiments, a crosslinkable entity is utilized in accordance with the present invention in a form or preparation having a viscosity suitable for topical application—e.g., with sufficient viscosity to maintain the applied crosslinkable entity in contact with the administration site for long enough to permit penetration and/or to otherwise permit distribution to the target site rather than simply dribbling off; in some such embodiments, the viscosity is within a range that permits the applied crosslinkable entity to flow into microstructures on the skin surface. In some embodiments, a crosslinkable entity is utilized in accordance with the present invention in a form or preparation having a viscosity suitable for administration by injection. In some embodiments, a suitable viscosity is a viscosity wherein the crosslinkable entity can be applied topically without rapidly running off, and/or can be rubbed into skin.

In some embodiments, the present disclosure provides a system comprising two or more crosslinkable entities, that interact with one another to form a crosslinked material (e.g., to provide a crosslinked material in situ at a target site on, at, in or below the epidermis, dermis or underlying hypodermis).

In some embodiments, at least one crosslinkable entity of a provided system comprises a polymer moiety linked with a crosslink moiety. In some such embodiments, at least one crosslinkable entity of the system does not comprise a polymer moiety linked with a crosslink moiety (i.e., comprises or consists of a crosslink moiety but not a polymer moiety); in some such embodiments, only one crosslinkable entity of a provided system comprises a polymer moiety linked with a crosslink moiety. Alternatively, in some embodiments, each crosslinkable entity of a provided system comprises a polymer moiety linked with a crosslink moiety; in some such embodiments, each crosslinkable entity of a provided system comprises the same polymer moiety.

Different crosslinkable entities of a provided system comprise complementary crosslink moieties so that the crosslinkable entities react to form a crosslinked material; in some embodiments, such crosslinking occurs absent any added catalyst.

In some embodiments, at least one crosslinkable entity of a provided system has a molecular weight (e.g., a number average molecular weight) above 500 daltons as described herein (e.g., has a molecular weight (e.g., a number average molecular weight) within a range of 1-1000 kDa). In some embodiments, at least one crosslinkable entity of a provided system has a molecular weight (e.g., a number average molecular weight) within a range of 1-10,000 kDa as described herein. In some such embodiments, at least one crosslinkable entity of the system does not have a molecular weight (e.g., a number average molecular weight) above 500 daltons as described herein (e.g., within a range of 1-400 daltons); in some such embodiments, only one crosslinkable entity of a provided system has such a high molecular weight (e.g., a number average molecular weight). Alternatively, in some embodiments, each crosslinkable entity of a provided system has such a high molecular weight (e.g., a number average molecular weight).

Polymer Moieties

In some embodiments, the present invention encompasses a crosslinkable entity, which comprises a polymer moiety and a crosslink moiety. In some embodiments, one or more of the polymer moieties are glycosaminoglycans or polysaccharides. In some embodiments, "polysaccharides" include dextran, starch or pectin. In some embodiments, one or more of the polymer moieties is dextran. In some embodiments, one or more of the polymer moieties is starch. In some embodiments, one or more of the polymer moieties is pectin. In some embodiments, "glycosaminoglycans" includes hyaluronic acid (HA), heparin sulfate, chondroitin sulfate, dermatan sulfate and keratin sulfate. In some embodiments, a polymer is hyaluronic acid.

In some embodiments, one or more of the polymer moieties is a synthetic polymer. In some embodiments, a "synthetic polymer" includes PEG, PEG-diamine, polyacrylic acid, N-(2-Hydroxypropyl) methacrylamide (HPMA), polycaprolactone (PCL) or poly(lactic-co-glycolic acid) (PLGA). In some embodiments, a synthetic polymer is PEG. In some embodiments, a synthetic polymer is PEG-diamine. In some embodiments, a synthetic polymer is polyacrylic acid. In some embodiments, a synthetic polymer is HPMA. In some embodiments, the synthetic polymer is PCL. In some embodiments, the synthetic polymer is PLGA.

In some embodiments, one or more of the polymer moieties is a polypeptide (e.g., a protein). In some embodiments, a useful polypeptide is or comprises collagen, gelatin, elastin, or a functional fragment thereof. In some embodiments, a polypeptide is or comprises collagen or a functional fragment thereof. In some embodiments, a polypeptide is gelatin. In some embodiments, a polypeptide is elastin.

In some embodiments, one or more polymer moieties included in a system as described herein is or comprises HA. In some embodiments, one or more polymer moieties included in a system as described herein is or comprises a glycosaminoglycan. In some embodiments, one or more polymer moieties included in a system as described herein is or comprises a polypeptide (e.g., a non-natural polypeptide and/or a synthetic or recombinant polypeptide). In some embodiments, a provided system includes a plurality of different crosslinkable entities comprising polymer moieties; in some such embodiments, the polymer moieties are selected from the group consisting of HA, proteoglycans, polypeptides, and combinations thereof.

Crosslink Moieties

As described herein, the present disclosure provides systems that include two or more crosslinkable entities that are compatible with one another in that they react to form a crosslinked material in situ.

Those skilled in the art are aware of a variety of chemical crosslinking systems. In many embodiments, the present disclosure utilizes crosslink chemistries that do not require an added catalyst.

In some embodiments, one or more of the crosslinkable entities of the system comprise a crosslink moiety. In some embodiments, a "crosslink moiety" is capable of participating in a click reaction.

A person of ordinary skill in the art will appreciate that a click reaction may be a reaction of two or more moieties which brings two or more substrates together and occurs under physiological pH. In some embodiments, a click reaction exhibits suitable kinetics (e.g. second-order rate constant ($k_2$) is about 9 $M^{-1}$ $s^{-1}$).

For example, in some embodiments, crosslink chemistries can include, but is not limited to, cycloadditions, nucleophilic substitution reactions, condensation reactions and nucleophilic addition reactions. In some embodiments, a click reaction is a [3+2] cycloaddition, a [4+2] cycloaddition or a [4+1] cycloaddition. In some embodiments, a click reaction is an azide-alkyne cycloaddition, a nitrone-olefin cycloaddition or a Diels-Alder reaction. In some embodiments, a click reaction is a Schiff reaction, a Michael-type addition, a nucleophilic substitution reaction on a haloacetate, a formation of a disulphide linkage, a free radical polymerization, a Huysgen reaction, phenols (tyramines) that spontaneously cross link after their enzymatic oxidation to catechols or a reaction between cyanobenzothiazole (CBT) and D-cysteine (CYS). In some embodiments, a click reaction is a reaction between CBT and D-cysteine. In some embodiments, a click reaction is a reaction between CBT and L-cysteine. In some embodiments, CBT can include analogs of CBT, e.g., isotopically labelled CBT. In some embodiments, CBT includes substituted analogs of CBT. In some embodiments, CYS can include analogs of CYS, e.g., isotopically labelled CYS. In some embodiments, CYS includes substituted analogs of CYS.

In some embodiments, the present disclosure appreciates that certain crosslink moieties may be particularly useful in in situ crosslinking contexts as described herein.

For example, in some embodiments, the present disclosure utilizes one or more crosslink moieties characterized by a desired degree of lipophilicity, for example, when linked with a particular polymer moiety. To give but one example, CBT represents a crosslinkable moiety that can be linked with a polymer moiety in a useful crosslinkable entity as described herein. Those skilled in the art, reading the present disclosure, will appreciate that, in some embodiments, lipophilicity of a crosslinkable entity comprising a particular polymer moiety may be adjusted through linkage of a plurality of hydrophobic moieties (e.g., hydrophobic crosslink moieties), which may be the same or different (and need not all be crosslink moieties).

Additionally, in some embodiments, a crosslink moiety is or comprises azide, alkyne, nitrone, olefin, diene, tetrazine, isocyanate, Michael acceptor, enone, aldehyde, amine, α-halo carbonyl moiety, maleimide, thiol, CBT, D-cysteine, acrylic residues, phenol, tyramine or catechol. In some embodiments, a crosslink moiety is or comprises D-cysteine.

In some embodiments, a crosslink moiety is or comprises L-cysteine. In some embodiments, a reactive moiety is or comprises CBT.

In some embodiments, at least one crosslink moiety included within a provided system may be utilized without linkage to a polymer moiety. That is, in some embodiments, at least one crosslinkable entity included within a provided system may consist of a crosslink moiety, or may comprise a crosslink moiety and at least one other moiety that is not a polymer moiety (which other moiety, as is clear from the present disclosure may, in some embodiments, be or comprise a hydrophobic moiety).

In some embodiments, a provided system may utilize a crosslink moiety that is or comprises, for example, a diamine, peptide, dithiol or dihydrazide. In some such embodiments, a diamine may be an ethylene diamine, e.g., a polyethylene glycol (PEG) diamine, etc; in some such embodiments, a dihydrazide may be an oxalic dihydrazide, malonic dihydrazide, succinic dihydrazide, glutaric dihydrazide, adipic dihydrazide or pimelic dihydrazide, etc. Without wishing to indulge in semantics, it is noted that certain such compounds could be described either as consisting of a crosslink moiety, or as comprising one or more crosslink moieties (e.g., each of which may be a single reactive atom or a small number of atoms), and a polymer moiety that may include only a very small (e.g., 2 or 3) number of "monomers" (and, in some instances where each such "monomer" might consist of only a few atoms). Regardless, those of ordinary skill in the art, reading the present disclosure, will appreciate that these compounds may be utilized in various embodiments, together with other crosslinking entities with complementary crosslink moieties as described herein.

Other Moieties

In some embodiments, a crosslinkable entity as described herein may comprise one or more moieties other than a polymer moiety or crosslink moiety, which other moiety(ies) may, in some embodiments, be covalently associated with a polymer moiety and/or with a crosslink moiety. In some embodiments, an "other" moiety may be releasably associated with the crosslinkable entity (e.g., via a cleavable bond; in some such embodiments, such cleavable bond may be cleaved at the target site).

For example, in some embodiments, a crosslinkable entity may comprise a drug moiety (which may, in some embodiments, itself be in a pro-drug form).

In some embodiments, a drug moiety is or comprises a synthetic or natural small molecule or biomolecule (e.g., a carbohydrate, a lipid, a nucleic acid, a polypeptide, or an analog or combination thereof).

In some embodiments, a drug moiety may be one that improves the appearance of the skin in one or more ways. For example, in some such embodiments, a drug moiety may brighten skin; clear breakouts; firm; improve cellular activity within skin; improve collagen synthesis; improve healing profile of a wound; improve pigmentation; improve skin barrier function; normalize healthy micoflora via topical pre-biotics; prevent damage (e.g., due UV exposure); reduce the appearance of scars; reduce inflammation; reduce itching; reduce redness; seal wounds; smooth, or treat burns or combinations thereof.

In some embodiments, a drug moiety may comprise an alpha-hydroxy acid (e.g., lactic, tartaric, or citric acid), an antioxidant (e.g., glutathione, an isoflavone, a polyphenol (e.g., resveratrol), or selenium), a beta-hydroxy acid (e.g., salicylic acid), a polyhydroxyl acid (e.g., gluconolactone or lactobionic acid), hydroquinone, natural skin lightening agents (e.g., Kojic acid), retinoids (e.g. retinoic acid, retinol, tretinoin or derivatives thereof), a ceramide, a peptide, an amino acid, a curcuminoid, vitamins (and derivatives thereof) (e.g., L-Ascorbic acid, vitamin B, niacinimide, and vitamin K), a sunscreen agent (e.g., oxybenzone, avobenzone, octisalate, octocrylene, homosalate, octinoxate, Meroxyl (SX and XL) or metallic oxides), coloring agents, pigments, or natural botanicals or combinations or prodrugs thereof.

In some embodiments, a drug moiety may comprise an anti-inflammatory (e.g., corticosteroids, non-steroidal anti-inflammatory drugs (crisaborole)), an antibiotic (e.g, clindamycin or ketoconazole), an antifungal (e.g., clotrimazole or ketoconazole), an anti-acne agent (e.g. retinoids or salicylic acid), an analgesics, an anticancer or antiproliferative agent, an agent which treats erythema (e.g., oxymetazoline hydrochloride), an agent which reduces subdermal fat (e.g., deoxycholate), a hair growth agent (e.g., finasteride), or combinations or prodrugs thereof.

Target Sites

Technologies as described herein are useful to provide crosslinked materials in situ at a target site. In some embodiments, a target site is or comprises (e.g., is on or within) a bodily tissue. Described herein are technologies for applying materials to an application site, such that a crosslinked material is provided (e.g., forms) at the target site.

For example, in some embodiments, a bodily tissue is or comprises epithelial tissue. In some embodiments, bodily tissue is or comprises connective tissue. In some embodiments, bodily tissue is or comprises nerve tissue. In some embodiments, a bodily tissue is or comprises muscle tissue. In some embodiments, a bodily tissue is or comprises tissue of the eye, tissue of the skin or subcutaneous tissue. In some embodiments, bodily tissue is or comprises subcutaneous fat, corneal epithelium or a mucous membrane.

As described herein, in many embodiments, materials (i.e., one or more crosslinkable entities) are administered to an application site such that the crosslinkable material is provided in situ at the target site (e.g., forms at the target site). In many embodiments, a target site is a site that is reached after application to a surface, e.g., a tissue surface. In some embodiments, a tissue surface is a surface of a tissue (e.g., skin, eye, or certain mucous membranes) that is exposed on a surface of an organism. In some embodiments, a tissue surface is a surface of an internal tissue that may, for example, be accessed or exposed by performance of a procedure (e.g., a medical procedure such as a surgical procedure including, for example, an orthoscopic procedure) or process applied to an organism.

In some embodiments, a target site is a target site on, at, in, or below the stratum corneum. In some embodiments, a target site is a site on, at, in, or below the epidermis. In some embodiments, a target site is a target site on, at, in, or below the dermis.

In some embodiments, a target site may be selected to be or comprise skin that has been damaged (e.g., due to a disease, disorder, or condition, or to a surgical, cosmetic, or dermatological treatment). In some embodiments, damaged skin may be or comprise laser (e.g., fractional laser) treated skin, intense-pulse-light-treated skin, microneedled skin, skin subjected to chemical peel treatment, skin exposed to dermabrasion, traumatically injured skin (including by surgery), skin suffering from a medical condition such as skin atrophy, extreme dryness, etc.

Alternatively or additionally, in some embodiments, a target site may be selected to treat skin that is wrinkled (e.g., crow's feet or other facial wrinkles), or otherwise shows signs of aging, or may be skin with respect to which additional plumpness and/or resilience is desired.

In some particular embodiments, skin of interest may be or comprise skin at a site selected from the group consisting of lips, lower lip, upper lip, tear troughs or other sites around the eyes (e.g., crow's feet), nasolabial folds, forehead, cheeks back of hands, ear lobes, knees, neck, décolletage, arms, legs, torso, buttocks, feet, and combinations thereof, including, for example, full face, etc.

In some embodiments, a target site may be or comprise adipose tissue (e.g., subcutaneous adipose tissue). Alternatively or additionally, in some embodiments, a target site may be or comprise a gland, such as a sebaceous gland and/or a serous (e.g., sweat) gland and/or a target site may be or comprise a vessel (e.g., a blood vessel) or duct (e.g., a sweat duct). Still further alternatively or additionally, in some embodiments, a target site may be or comprise one or more specific cell populations, for example, that may be localized within one or more skin layers; for example, in some such embodiments, a relevant cell population may be or comprise particular stem cells or cell populations associated with a state of disease or injury. In some particular embodiments, a target site may be or comprise pigment producing cells. In some particular embodiments, a target site may be or comprise one or more hair follicles. In some particular embodiments, a target site may be or comprise one or more nerve cells or nerves.

Administration of Provided Systems

As described herein, the present disclosure provides systems that include at least first and second crosslinkable entities, which systems are administered to a skin site. In some embodiments, both crosslinkable entities are administered to the same site; in some embodiments, each may be administered to a different site so long as both ultimately arrive at a target site of interest, so that a crosslinked material, generated by reaction of the first and second crosslinkable entities, is formed or otherwise provided in situ at the target site.

In some embodiments, at least one crosslinkable entity is administered topically (i.e., to a skin surface). In some embodiments, at least one crosslinkable entity is administered parenterally (e.g., by injection into a target site or to a location from which it penetrates into the target site).

In some embodiments, a provided system is administered to a subject's face (e.g., full face and/or specific targets of a subject's face such as to lips, lower lip, upper lip, tear troughs, crow's feet, nasolabial folds, forehead, cheeks or combinations thereof). In some embodiments, a provided system is administered to a non-facial site (e.g., knees, neck, décolletage, legs, arms, torso, buttocks or feet). In some embodiments, a provided system is administered to hands (e.g., to the back of a hand). In some embodiments, a provided system is administered to ear lobes.

In some embodiments, first and second crosslinkable entities are administered simultaneously. For example, in some embodiments, first and second crosslinkable entities may be combined prior to or as they are administered. In some embodiments, such combination may be referred to as a pre-mix, and may be prepared a period of time prior to administration; typically, such a pre-mix is prepared within about 1 minute of administration.

In some embodiments, site of administration is prepared prior to administration of a crosslinkable entity. In some embodiments, site of administration is prepared by washing site with tepid water and soap. In some embodiments, site of administration is prepared through tape stripping. In some embodiments, tape stripping comprises application of Scotch semi-transparent tape to site of administration. In some embodiments, tape stripping further comprises removal of the previously applied of Scotch semi-transparent tape from site of administration. In some embodiments, tape stripping is repeated until site of administration glistens. In some embodiments, tape stripping is repeated at least 40 times.

In some embodiments, first and second crosslinkable entities are administered sequentially; in some such embodiments, a period of time separates administration of the first and second crosslinkable entities. In some embodiments, such a period of time is about 30 seconds, about 1 minute, about 2 minutes, about 3 minutes, about 4 minutes, about 5 minutes, about 10 minutes, about 30 minutes, about 1 hours, about 6 hours, about 12 hours, or more. In some embodiments, such a period of time is about 2 hours. In some embodiments, such a period of time is less than about 12 hours, less than about 6 hours, less than about 1 hour, less than about 20 minutes, less than about 10 minutes, less than about 5 minutes, less than about 2 minutes, or less than about 1 minute.

In some embodiments, site of application is covered after application of a crosslinkable entity. In some embodiments, site of application is covered with Tegaderm™ type film after application of a crosslinkable entity.

In some embodiments, a period of time between administration of first and second crosslinkable entities is sufficient to permit substantial penetration of the first-administered crosslinkable entity before the second crosslinkable entity is administered. In some embodiments, the period of time is sufficient so that at least about 1%, at least about 2%, at least about 5%, at least about 10%, or at least about 20% of the first-administered crosslinkable entity has penetrated prior to administration of the second-administered crosslinkable entity. In some embodiments, the period of time is sufficient such that the first agent has not degraded and/or been cleared from skin. Kinetics and/or extent of penetration for a particular crosslinkable entity may be determined, for example, as described herein, including through use of a model system (e.g., porcine skin); the relevant period of time may be selected in light of such determination.

In some embodiments, skin will be treated with water after administration of a system.

In some embodiments, a system is administered daily. In some embodiments, a system is administered at least once daily. In some embodiments, a system is administered at least twice daily. In some embodiments, a system is administered a 1-5 times daily. In some embodiments, a system is administered a 3-5 times daily. In some embodiments, a system is administered every 3 days. In some embodiments, a system is administered every 7 days. In some embodiments, a system is administered about every 15 days. In some embodiments, a system is administered about every 30 days. In some embodiments, a system is administered about every 60 days. In some embodiments, a system is administered about every 90 days.

In some embodiments, a provided system includes a chemical entity which improves skin penetration for a crosslinkable entity. In some embodiments, the chemical entity is administered simultaneously with a crosslinkable entity. In some embodiments, the chemical entity and the crosslinkable entity are administered at different times.

In some embodiments, a provided system comprises one or both of a penetration inhibitor (e.g., which may interact with and/or otherwise retard penetration of a crosslinkable entity) and a cross-link inhibitor (e.g., which may block one or more features of a crosslinkable entity or crosslink moiety, or otherwise interfere with reaction of crosslink moieties to generate a crosslink); in some such embodiments, such an inhibitor may be removed (e.g., via diffusion, washing, degradation) prior to, during, upon or after administration of the crosslinkable entity.

In some embodiments, one or more crosslinkable entities is administered as or in a sustained-release formulation. In some embodiments, one or more crosslinkable entities is encapsulated within a matrix or particle (e.g., a nanoparticle). In some embodiments, one or more crosslinkable entities is provided as or in an emulsion or dispersion.

In some embodiments, crosslinkable entities whose crosslink moieties interact to form crosslinks in the crosslinked material are administered in relative amounts (e.g., are formulated for administration in relative amounts) so that complementary crosslink moieties are present in stoichiometric amounts. Alternatively, in some embodiments, such crosslinkable entities are administered in relative amounts so that one of a pair of complementary crosslink moieties is present in molar excess relative to the other; in some such embodiments, such molar excess is within a range of 1.1:1-10,000:1. In some embodiments, molar excess of the relative amounts of crosslinkable entities is within a range of 1.1:1-2:1. In some embodiments, molar excess of the relative amounts of crosslinkable entities is within a range of 1.1:1-10:1. In some embodiments, molar excess of the relative amounts of crosslinkable entities is within a range of 1.1:1-100:1. In some embodiments, molar excess of the relative amounts of crosslinkable entities is within a range of 1.1:1-1,000:1.

In some embodiments, a formulation comprises about 0.001% w/w to about 5.00% w/w of a crosslinkable entity. In some embodiments, a formulation comprises about 0.01% w/w to about 5.00% w/w of a crosslinkable entity. In some embodiments, a formulation comprises about 0.1% w/w to about 5.00% w/w of a crosslinkable entity. In some embodiments, a formulation comprises about 1% w/w to about 5.00% w/w of a crosslinkable entity. In some embodiments, a formulation comprises about 1% w/w to about 3% w/w of a crosslinkable entity. In some embodiments, a formulation comprises about 2% w/w of a crosslinkable entity. In some embodiments, a formulation comprises PBS and about 2% w/w of a crosslinkable entity.

Topical Application

In some embodiments, at least one crosslinkable entity of a provided system is provided topically, e.g., to a site on skin, e.g., on a skin surface.

In some embodiments, a formulation for topical administration may be or comprise a cream, gel, liquid, lotion, mask, matrix, mist particle, paste, patch, powder, serum, solid, spray (or collection thereof), or a combination thereof. In some embodiments, a formulation for topical administration may be or comprise a mask or serum.

In some embodiments, a formulation for topical administration may comprise antioxidants, buffers, chelating agents, clarity enhancers, emollients, emulsifiers, gelling agents, humectants, lubricants, moisturizers, pH adjusters, preservatives, protectants, prebiotics, probiotics, rheological modifiers, sensory modifiers, soothing agents (e.g., soothing plant serums), stabilizers, sunscreens (e.g., inorganic broad-spectrum sunscreen), or thickening agents.

In some embodiments, topical application does not involve administration or application of penetration enhancer (e.g., a chemical or physical abrading or disrupting agent and/or an electrical current and/or an electrical or magnetic field, etc).

In some embodiments, the first and second crosslinkable entities are separated by chemical means. In some such embodiments, a crosslinkable entity is encapsulated in, for example, micelles, liposomes, etc.

In some embodiments, the system is administered and the crosslinkable entity is released over a period of time.

In some embodiments, the system comprises a transdermal patch formulated to facilitate time release of a crosslinkable entity. A person of skill in the art will appreciate a transdermal patch can be single layer agent-in patch, multilayer agent-in patch, reservoir, or matrix. As discussed below, in some embodiments, a patch may comprise microneedle(s) (some or all of which may, in some embodiments, as is known in the art, be solid protrusions, and some or all of which may, in some embodiments, as is known in the art, be hollow).

Those skilled in the art, reading the present disclosure, will appreciate that in some embodiments, delivery may be achieved or enhanced by topical administration to a site that is or has been damaged, e.g., through exposure to one or more of laser (e.g., fractional laser) treatment, intense-pulse-light-treatment, microneedling, chemical peel treatment, dermabrasion, etc, each of which may, in some embodiments, be or have been administered before, during, or after, topical application of a system as described herein.

Injection

In some embodiments, at least one crosslinkable entity is administered by injection. In some embodiments, injection is below the surface of skin. In some embodiments, injection is into a target site. In some embodiments, injection is into a site from which the injected crosslinkable entity penetrates to the target site.

In some embodiments, injection may comprise application of force or pressure (e.g., via a syringe) so that delivery is achieved, e.g., through a needle, cannula, or other passage.

In some embodiments, injection may be via microneedles (e.g., that may be associated with a patch). For example, in some embodiments, one or more crosslinkable entities, or combinations thereof may be administered through microneedles (e.g., as a liquid); alternatively or additionally, in some embodiments, one or more crosslinkable entities, or combinations thereof, may be disposed within one or more microneedles, which may dissolve or degrade upon or after application. Those skilled in the art will appreciate that use of dissolving or degrading microneedle(s) may be particularly useful or desirable for delivery of relatively viscous materials (e.g., partially or wholly formed crosslinked material as described herein). In some embodiments, one or more crosslinkable entities may be disposed in a microneedle; e.g., in a lumen (e.g., bore) thereof; in some such embodiments, the one or more crosslinkable entities (or a crosslinked material formed therefrom) may be released by injection through the lumen, and/or by dissolution or degradation of the microneedle (e.g., of its walls). In some embodiments, one or more crosslinkable entities may be integrally formed with a microneedle; in some such embodiments, the microneedle may be otherwise formed of a material that dissolves or degrades upon or after application, thereby releasing the one or more crosslinkable entities, or a crosslinked material formed therefrom.

In some embodiments, injection may be by a dual bore syringe or needle. In some such embodiments, first and second crosslinkable entities are maintained in separate compartments of the syringe or needle at least until administration. In some embodiments, they are combined during administration; in other embodiments, they are maintained separately during administration (i.e., each is separately administered, optionally at times separated by a time period as described herein).

In some embodiments, injection is via a needle having a bore size about 26 gauge to about 30 gauge.

In some embodiments, skin has been pretreated prior to (e.g., promptly or immediately prior to) administration of a system. In some embodiments, skin pretreatment is accomplished by administration or application of a permeabilizing agent or device. In some embodiments, skin pretreatment comprises one or more of application of an abrasive cleanser or chemical peel, dermablation, electroporation, iontophoresis, low-frequency sonophoresis, mirconeedling. In some embodiments, skin is abraded prior to administration of a system. In some such embodiments skin is abraded with microneedles and/or fraction lasers prior to administration of the system. In some embodiments, a crosslinkable entity will be administered after (e.g., promptly or immediately after) pretreatment of skin with microneedles.

Kits

In some embodiments, the present disclosure provides kits that comprise systems described herein.

In some embodiments, a provided kit comprises a plurality of containers or vessels, including containers that separately house first and second crosslinkable entities.

In some embodiments, a provided kit comprises at least one container or vessel that includes a plurality of separate compartments (e.g., a dual-bore syringe or needle—or dual chamber package with a mixing chamber prior to dispensing); in some embodiments first and second crosslinkable entities are separately housed in such compartments.

In some embodiments, the present disclosure provides one or more containers, vessels, or compartments in which a first or second crosslinkable entity as described herein is disposed. In some such embodiments, the disposed crosslinkable entity is present in dry form; in some such embodiments, the crosslinkable entity is present in liquid form. In some embodiments, the disposed crosslinkable entity has been stored for a period of time (e.g., for at least 1 day, 1 week, 1 month, 3 months, 6 months or more); in some such embodiments, the stored composition has been stable over the period of storage time, in that at least about 80%, 85%, 90%, 95%, 96%, 97%, 98%, 99% or more of the crosslinkable entity remains undegraded. In some embodiments, the stored composition has been stable over the period of storage time, in that at least about 50%, 65%, 70%, 75% or more of the crosslinkable entity remains undegraded.

Characterization

Those skilled in the art, reading the present specification, will appreciate that it may be desirable to characterize one or more features of crosslinkable entities, and/or of components or combinations thereof and/or of crosslinked material(s) they produce, for example when designing (e.g., selecting appropriate components of) or producing a provided system and/or when monitoring or assessing a preparation thereof. Alternatively or additionally, in some embodiments, it may be desirable to assess one or more features of a provided system as administered, for example in order to monitor a subject or treatment thereof.

In some embodiments, first and second crosslinkable entities of a system when combined in vitro under physiological conditions, the first and second crosslinkable entities react with one another within a time period less than about 60 minutes at 37° C. to form a crosslinked material. Properties of such crosslinked material can be modulated through selection of the crosslinkable entities that generate it, and can represent characteristic traits of the particular crosslinked material provided by the present invention. In some embodiments, a storage modulus of a crosslinked material is within a range of 50 Pa-10 kPa. In some embodiments, a storage modulus of a crosslinked material is within a range of 50 Pa-1 kPa. In some embodiments, a storage modulus of a crosslinked material is within a range of 50 Pa-500 Pa. In some embodiments, a storage modulus of a crosslinked material is within a range of 50 Pa-100 Pa. In some embodiments, a storage modulus of a crosslinked material is within a range of 100 Pa-10 kPa. In some embodiments, a storage modulus of a crosslinked material is within a range of 500 Pa-10 kPa. In some embodiments, a storage modulus of a crosslinked material is within a range of 1 kPa-10 kPa. In some embodiments, a storage modulus of a crosslinked material is within a range of 5 kPa-10 kPa. In some embodiments, a storage modulus of a crosslinked material is within a range of 500 Pa-5 kPa. In some embodiments, a storage modulus of a crosslinked material is within a range of 500 Pa-1 kPa.

In some embodiments, mass loss of a crosslinked material by degradation of less than 20% over 3 days in physiological buffer. In some embodiments, mass loss of a crosslinked material by degradation of less than 10% over 3 days in physiological buffer. In some embodiments, mass loss of a crosslinked material by degradation of less than 5% over 3 days in physiological buffer.

In some embodiments, a degree of crosslinked material swelling upon hydration is characteristic property of a crosslinked material. In some embodiments, degree of crosslinked material swelling will be measured based on the mass ratio between dried crosslinked material and fully swollen crosslinked material which has reached equilibrium with an external aqueous buffer ($Q=m_{swollen}/ma_{dry}$). In some embodiments, a ratio between dried crosslinked material and fully swollen crosslinked material will be within a range of 50-1000. In some embodiments, a ratio between dried crosslinked material and fully swollen crosslinked material will be within a range of 100-1000. In some embodiments, a ratio between dried crosslinked material and fully swollen crosslinked material will be within a range of 500-1000. In some embodiments, a ratio between dried crosslinked material and fully swollen crosslinked material will be within a range of 750-1000. In some embodiments, a ratio between dried crosslinked material and fully swollen crosslinked material will be within a range of 50-100. In some embodiments, a ratio between dried crosslinked material and fully swollen crosslinked material will be within a range of 50-250. In some embodiments, a ratio between dried crosslinked material and fully swollen crosslinked material will be within a range of 50-500. In some embodiments, a ratio between dried crosslinked material and fully swollen crosslinked material will be within a range of 50-750. In some embodiments, a ratio between dried crosslinked material and fully swollen crosslinked material will be within a range of 250-750. In some embodiments, a ratio between dried crosslinked material and fully swollen crosslinked material will be within a range of 400-600.

In some embodiments, time in which formation of the crosslinked material occurs will be determined by the time from when the first and second crosslinkable entities of the system when are combined until the dynamic storage modulus (G') becomes larger than the loss modulus (G"). In some embodiments, a first and second clickable entity will form a crosslinked material within 1 second. In some embodiments, a first and second clickable entity will form a crosslinked material within 10 seconds. In some embodiments, a first and second clickable entity will form a crosslinked material within 1 minute. In some embodiments, a first and second clickable entity will form a crosslinked material within 10 minutes. In some embodiments, a first and second clickable entity will form a crosslinked material within 30 minutes. In some embodiments, first and second clickable entity will form a crosslinked material within 60 minutes.

In Vitro Characterization

In some embodiments, characterization may involve application of a provided system to a model skin system (e.g., to porcine skin).

In some embodiments, characterization may involve monitoring one or more features of skin penetration. In some embodiments, amount of a crosslinkable entity which penetrates the skin 0.5-2 days after topical application on porcine skin will be quantified, for example, after solubilizing the skin using enzymes and/or other solubilizing agents. In some embodiments, amount of a crosslinkable entity which penetrates the skin at least 0.5 days after topical application on porcine skin will be quantified after solubilizing the skin using enzymes and/or other solubilizing agents. In some embodiments, amount of a crosslinkable entity which penetrates the skin less than 2 days after topical application on porcine skin will be quantified after solubilizing the skin using enzymes and/or other solubilizing agents. In some embodiments, amount of a crosslinkable entity that comprises a polymer moiety and a crosslink moiety which penetrates after topical application on porcine skin exceeds the amount of an entity which comprises the same polymer moiety and does not comprise the crosslink moiety. In some embodiments, a crosslinkable entity comprises HA and the amount of crosslinkable entity which penetrates after topical application on porcine skin will exceed the amount of natural HA at the same molecular weight (e.g., number average molecular weight) which penetrates the skin. Preferably, in some embodiments, amount of the crosslinkable entity that comprises HA which penetrates after topical application on porcine skin will exceed the natural amount of HA already found in the skin (natural amount of HA already found in porcine skin=~100-800 ug/g dry tissue).

In some embodiments, the depth of penetration of crosslinked material within the porcine skin is measured by shining ultraviolet light on the target site. In some embodiments, the presence of crosslinked material in the porcine skin will be determined by observation of fluorescence upon shining ultraviolet light on the target site.

In some embodiments, presence of the crosslinked material at the target site will be observable after a period of time (e.g., 1, 2, 3, 4, 5, 6, 7, 8, 9, 10, 11, 12, 13, 14, 15, 20, 25, 30 or more days). In some embodiments, presence of the crosslinked material at the target site will be observable after about 3.5 days. In some embodiments, presence of the crosslinked material at the target site will be observable after about 9 days.

In Vivo Characterization

Upon administration of the system described herein, attributes of the target site and/or site of administration, i.e. skin, will be evaluated at an appropriate time period for improvement as compared to the skin attribute prior to administration of the system. In some embodiments, skin attribute includes wrinkles, radiance, firmness, moisture content, skin thickness, elasticity, and skin smoothness. In some embodiments, improvement includes repair to atrophic skin or scars. In some embodiments, administration of the system results in fibroblast activation and/or enhanced collagen synthesis within the target sight of the skin.

In some embodiments, improvement of the skin will be measured by the Global Aesthetic Improvement Scale (GAIS). A person of skill in the art will appreciate the GAIS can be determined using the following rating scale:
1=very much improved
2=much improved
3=improved
4=no change
5=worse In some embodiments, a majority of subjects will observe >1 improvement on the GAIS. In some embodiments, a majority of subjects will observe >2 improvement on the GAIS. In some embodiments, a majority of subjects will observe >3 improvement on the GAIS. In some embodiments, a majority of subjects will observe about 1 to about 2 improvement on the GAIS. In some embodiments, a majority of subjects will observe about 1 to about 3 improvement on the GAIS. In some embodiments, a majority of subjects will observe about 1 improvement on the GAIS. In some embodiments, a majority of subjects will observe about 2 improvement on the GAIS. In some embodiments, a majority of subjects will observe about 3 improvement on the GAIS.

In some embodiments, improvement in skin will be measured using the Modified Fitzpatrick Wrinkle Scale (MFWS). A person of skill in the art will appreciate the MFWS can be determined using the following rating scale:
Class 0—No wrinkle. No visible wrinkle; continuous skin line.
Class 0.5—Very shallow yet visible wrinkle.
Class 1—Fine wrinkle. Visible wrinkle and slight indentation.
Class 1.5—Visible wrinkle and clear indentation. 01-mm wrinkle depth.
Class 2—Moderate wrinkle. Clearly visible wrinkle, 1- to 2-mm wrinkle depth.
Class 2.5—Prominent and visible wrinkle. More than 2-mm and less than 3-mm wrinkle depth.
Class 3—Deep wrinkle. Deep and furrow wrinkle; more than 3-mm wrinkle depth.

In some embodiments, a subject's wrinkles will decrease at least 0.5 on the MFWS. In some embodiments, a subject's wrinkles will decrease between 1 and 0.5 on the MFWS. In some embodiments, a subject's wrinkles will decrease between 1.5 and 0.5 on the MFWS. In some embodiments, a subject's wrinkles will decrease between 2 and 0.5 on the MFWS. In some embodiments, a subject's wrinkles will see a decrease of between 2.5 and 0.5 on the MFWS. In some embodiments, a subject's wrinkles will decrease between 3 and 0.5 on the MFWS.

In some embodiments, subject's skin will be assessed for improvements in smoothness, radiance or firmness.

In some embodiments, moisture content of the skin can be monitored. In some embodiments, moisture content of skin will be higher as compared to untreated skin as determined by methods known in the art. In some embodiments, moisture content of skin will be determined by Corneometer CM 825. In some embodiments, moisture content of skin will be >20% higher after administration of the system at day 7.

In some embodiments, a provided system is used to treat a person exhibiting abnormal transepidermal water loss (TEWL). A person of skill in the art will understand that abnormal TEWL can be the result of skin damage caused by, for example, burns, certain chemicals, pathological conditions (e.g. eczema), physical abrasion, tape stripping, ultraviolet radiation, or combinations thereof. In some embodiments, the level of TEWL of treated skin will be lower as compared to untreated skin as determined by methods known in the art. In some embodiments, the level of TEWL of treated skin will be statistically lower as compared to a baseline level as understood by methods known in the art. In some embodiments, TEWL will be measured by Tewameter™ 300 meter (Courage-Khazaka Electronics). In some embodiments, TEWL will be measured by Tewameter™ Nano (Courage-Khazaka Electronics). In some embodiments, TEWL will be measured by Tewameter Triple™ 330T (Courage-Khazaka Electronics). In some embodiments, TEWL will be measured by Invitro Tewameter VT310 (Courage-Khazaka Electronics). In some embodiments, TEWL of treated skin will be >10% lower after administration of the system at day 7.

In some embodiments, skin will assessed for improvements in skin smoothness. In some embodiments, skin after administration of the system will be smoother than skin prior to administration of the system. In some embodiments, skin's smoothness will be assessed using Surface Evaluation of Living Skin (SELS). In some embodiments, skin will be assessed using phaseshift rapid in vivo measurement of skin (PRIMOS). In some embodiments, skin will be assessed by 3D Skin profilometry via Canfield Primos. In some embodiments, skin will be assessed using the Lemperle wrinkle scale. In some embodiments, skin will be assessed using a 7-point subject satisfaction scale. In some embodiments, skin will be assessed using the Oral commissures. In some embodiments, skin will be assessed using Allergan Skin Roughness scale.

In some embodiments, skin will be assessed to determine presence and/or extent of crosslinked material within the skin. In some embodiments, presence and/or of crosslinking material within the skin will be measured using near infrared (NIR) spectroscopy, confocal microscopy, a integrating sphere spectrophotometer, or will be determined using Viscoelastic deformation (VED, mm), elastic deformation (ED, mm), ultimate deformation (UD, mm), and pressure-deformation ratio methods. In some embodiments, presence and/or of crosslinked material within the skin is measured by shining ultraviolet light on the target site. In some embodiments, presence and/or of crosslinked material in the skin will be determined by observation of fluorescence upon shining ultraviolet light on the target site.

In some embodiments, presence of the crosslinked material at the target site will be observable after a period of time (e.g., 1, 2, 3, 4, 5, 6, 7, 8, 9, 10, 11, 12, 13, 14, 15, 20, 25, 30 or more days). In some embodiments, presence of the crosslinked material at the target site will be observable after about 2 days. In some embodiments, presence of the crosslinked material at the target site will be observable after about 9 days. In some embodiments, presence of the crosslinked material at the target site will be observable after about 11 days. In some embodiments, presence of the crosslinked material at the target site will be observable after about 20 days. In some embodiments, presence of the crosslinked material at the target site will be observable after about 30 days.

EXEMPLIFICATION

The present Examples describe, among other things, certain strategies that may be used to characterize and/or assess crosslinkable entities (and/or components and/or combinations thereof) as described herein, and/or the crosslinked materials formed by their reaction. Such strategies (or their equivalents as will be appreciated by those skilled in the art reading the present disclosure) may be used to assess potential crosslinkable entities, components (e.g., moieties), or combinations thereof, and/or crosslinked materials (e.g., gels) they form, for suitability for use in accordance with the present disclosure. In some embodiments, therefore, the present disclosure provides technologies for characterizing and/or selecting useful moieties, crosslinkable entities, and/ or combinations thereof.

Example 1. Synthesis of Crosslinkable Entities

First Crosslinkable Entity Synthesis: HA-gly-CBT
Step 1— CBT-glycine:

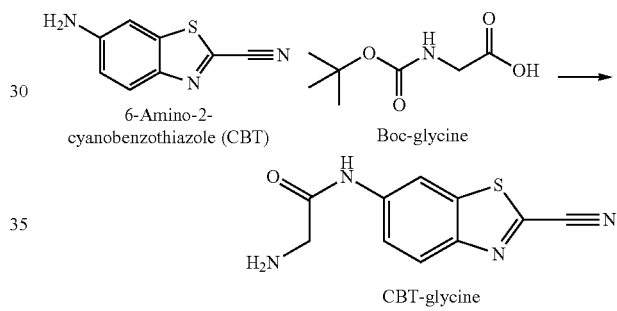

A mixture of Boc-glycine (1.4 equiv.), DIPEA (2.1 equiv.), and TBTU (1.4 equiv.) in anhydrous DMF (~40 mg Boc-glycine/mL) is stirred for 30 minutes at room temperature. A solution of CBT (1 equiv.) in anhydrous DMF (~100 mg CBT/mL) and DIPEA (1.4 equiv.) is added to the mixture. The reaction is stirred at room temperature under nitrogen for 4 h. Solvent is removed via rotary evaporation, and the crude product is dissolved in ethyl acetate and the organic layer is washed sequentially with water, a saturated sodium bicarbonate aqueous solution, and then brine. Boc-gly-CBT is then further isolated with flash chromatography with 3:1 to 1:1 hexanes:ethyl acetate. Boc-deprotection is accomplished by stirring Boc-gly-CBT in 1:1 TFA:DCM for 1 h. Solvent is then removed via rotary evaporation.
Step 2— HA-gly-CBT:

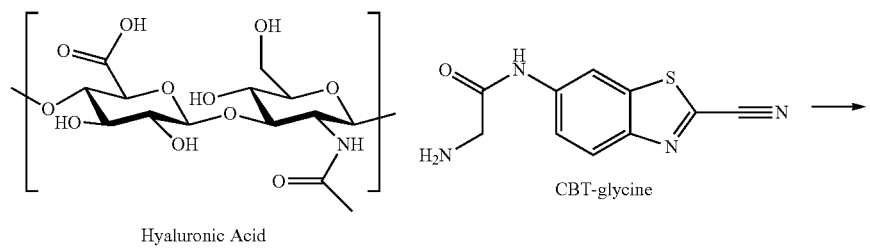

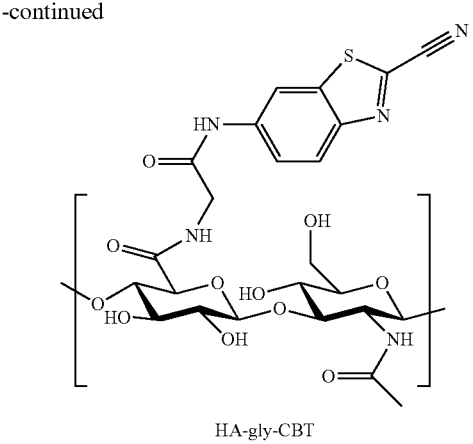

HA-gly-CBT

Figure 2:
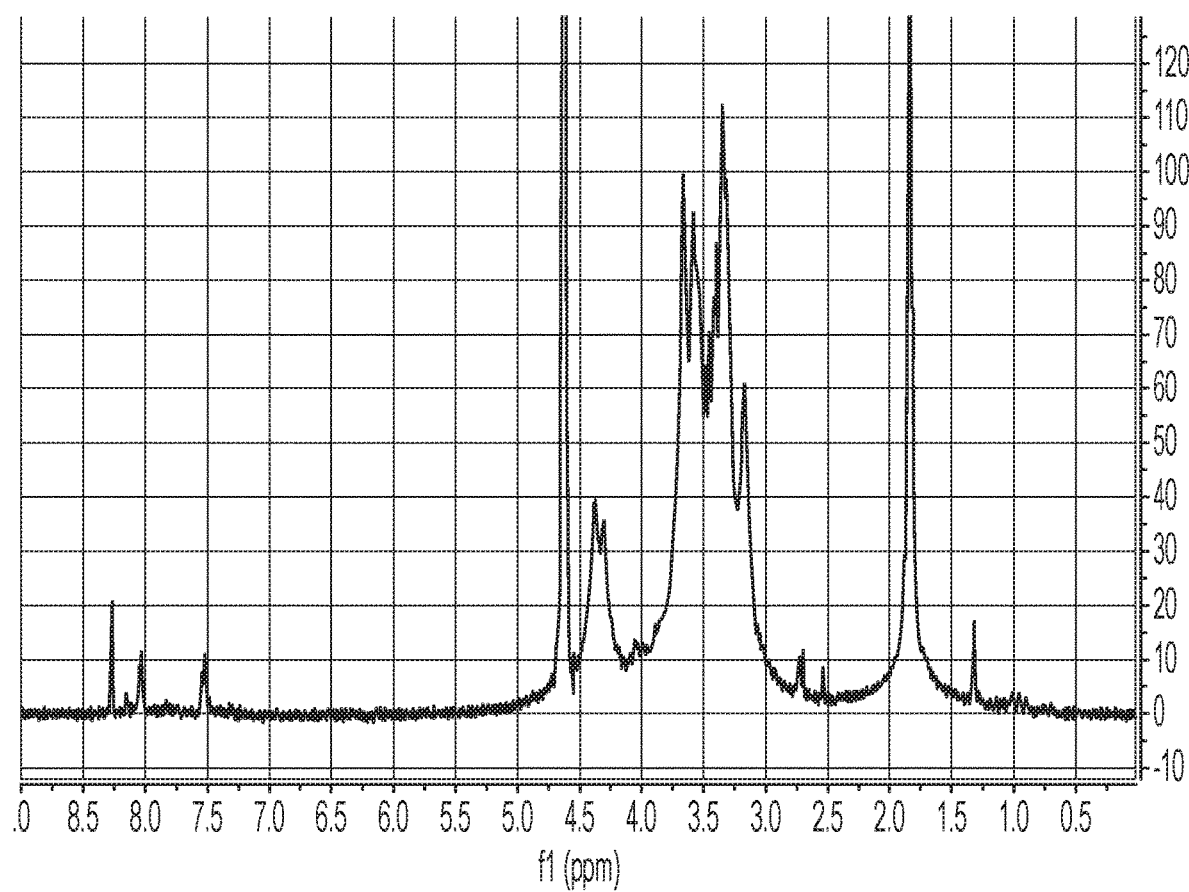
FIG. 2 illustrates $^1$H NMR of HA-gly-CBT in $D_2O$ from Example 1.

After dissolving HA (1 equiv.) into 1:1 DMSO:DI water (10 mg/mL), N-Hydroxysulfosuccinimide sodium salt (sulfo-NHS, 0.18 equiv.), N-(3-Dimethylaminopropyl)-N′-ethylcarbodiimide hydrochloride (EDC, 0.18 equiv.), and gly-CBT (0.18 equiv.) are added sequentially to the reaction mixture. After reacting for 24 h at room temperature, HA-gly-CBT is purified through repeat precipitation from ethanol followed by dialysis for 24 h. HA-gly-CBT is then dried via lyophilization. The proton NMR spectrum of HA-gly-CBT is depicted in FIG. 2.

Synthesis of HA-gly-CBT with Different Molecular Weights

Figure 3:
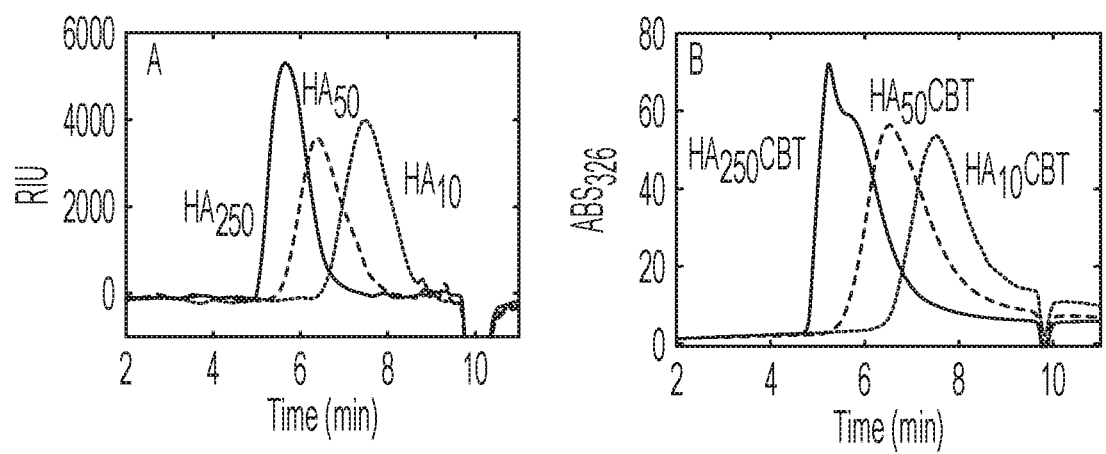
FIG. 3 illustrates gel permeation chromatography (GPC) analysis of modified HA. Refractive index reading of unmodified HA (with average molecular weights of 10, 50, and 250 kDa) prior to conjugation is illustrated in FIG. 3A, and UV absorbance reading (326 nm) of modified HA (HA-gly-CBT, with average molecular weights of 10, 50, and 250 kDa) is illustrated in FIG. 3B.

HA-gly-CBT was synthesized with different degrees of CBT functionalization by changing stoichiometry of the reactants. Further, HA-gly-CBTs of different molecular weights were synthesized using the two-step synthesis described herein, by starting with HA of different molecular weights (~10, 50, and 250 kDa purchased from Creative PEG works). Gel permeation chromatography (GPC) was used to verify the synthesis of the crosslinkable entity with different molecular weights. GPC analysis was performed on an Agilent 1100 HPLC using DAD and RI detectors in series, with an Agilent PL aquagel-OH MIXED-M column (8 um 300×7.5 mm). A mobile phase of 0.2 M NaNO$_3$ in water was used at a flow rate of 1 mL/min. The GPC analysis of three crosslinkable entities prepared using the 10, 50, and 250 kDA HA is depicted in FIG. 3.

Synthesis of Different Variants of HA-CBT

Figure 4:
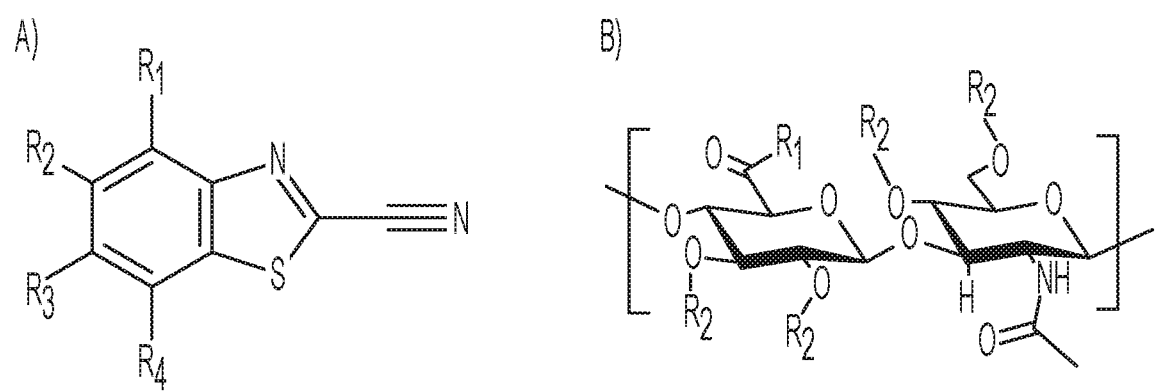
FIG. 4 illustrates the chemical structure of certain derivatives of CBT and HA (A and B, respectively).
Figure 5:
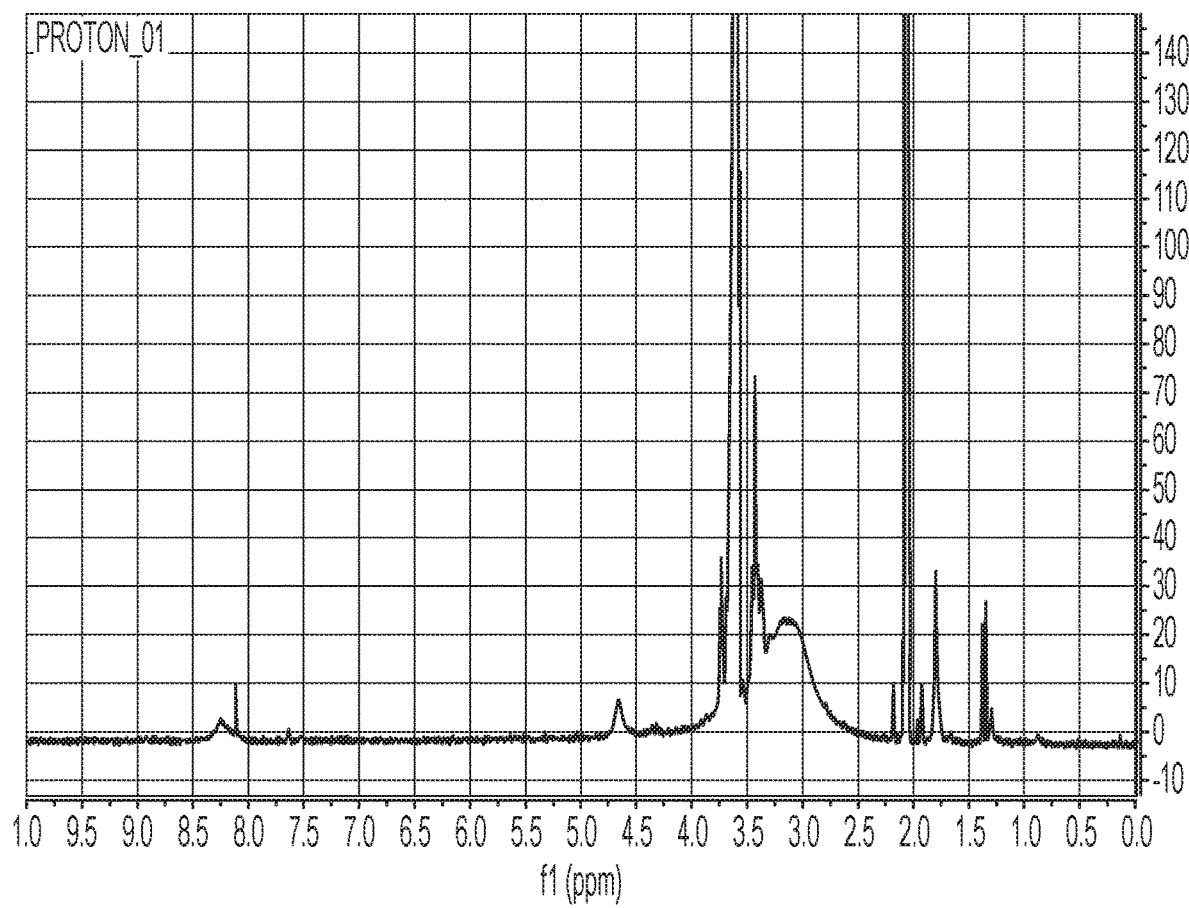
FIG. 5 illustrates $^1$H NMR of Cys-PEG-Cys in deuterated acetone from Example 1.

In some embodiments, a first crosslinking entity can be an HA derivative functionalized with a CBT derivative. For example, in some embodiments, a CBT derivative (other than 6-amino-2-cyanobenzothiazole) can be conjugated to HA, such as 6-hydroxybenzothiazole-2-carbonitrile or another chemical derivative of the structure shown in FIG. 4a. In some embodiments, this CBT derivative can be further derivatized prior to conjugation to HA with a chemical linker to facilitate conjugation to HA. In some embodiments, this chemical linker can be an amino acid among other chemical groups. In some embodiments, the CBT derivative can be conjugated to the carboxylic acid (R1), alcohols (R2), or another chemical group on HA as shown in FIG. 4b.

In some embodiments, lipophilicity and/or skin penetration of an HA-CBT derivative can be increased by conjugating one or more other chemical moieties to an HA backbone, for example using one or more CBT derivatives that may be more hydrophobic than is CBT itself (and/or than is the HA itself), among other chemical modifications.

In some embodiments, an HA-CBT comprises (e.g., is conjugated with) one or more chemical moieties (e.g., one or more hydrophobic moieties) such as for, example, a fatty acid.

In some embodiments, one or more moieties (e.g., hydrophobic moieties, e.g., CBT derivaties and/or fatty acid moieties) may be conjugated to an alcohol (R2) on the backbone of HA. In some embodiments, before or after such conjugation, HA can be oxidized, converting a fraction of the alcohols (R2) to aldehydes.

In some embodiments, conjugation of a moiety to HA (e.g., to an alcohol on the HA backbone) may be via a linker; in some such embodiments, the linker can be a hydrophobic amino acid, or other hydrophobic chemical moiety.

In some embodiments, one or more moieties that is conjugated to an HA (or other polymer moiety) as described herein may be modified (e.g., functionalized) before or after such conjugation. To give but one particular embodiment, in some embodiments, some or all of (e.g., a fraction of) CBT or CBT derivative moieties conjugated to HA can be further functionalized, e.g., by reacting the nitrile group with a hydrophobic cysteine derivative or another aminothiol, such as cysteamine.

Second Crosslinkable Entity Synthesis: Cys-PEG-Cys

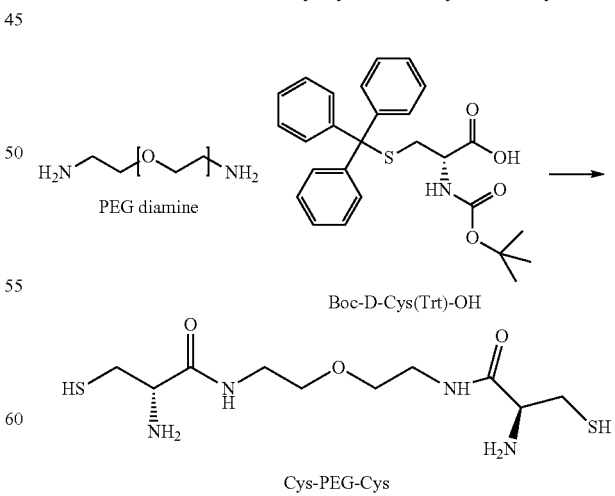

Cys-PEG-Cys

Cys-PEG-Cys is synthesized by conjugating the carboxylic acid on cysteine (Cys) to the amines on PEG diamine. A mixture of N-Boc-S-trityl-D-cysteine (2.4 equiv.) and 1,1'-Carbonyldiimidazole (CDI, 3.0 equiv.) in anhydrous DMF (~55 mg N-Boc-S-trityl-D-cysteine/mL) is stirred for 30 minutes at room temperature. A solution of PEG diamine (~2000 Da; 1 equiv.) in anhydrous DMF (~125 mg PEG diamine/mL) is then added to the reaction mixture. After reacting for 4 h at room temperature, DMF is removed with rotary evaporation and the polymer is precipitated 2× into 1:1 diethyl ether:n-hexane. The Boc- and trityl-deprotection is accomplished by adding the polymer to a solution of 0.85:0.10:0.05 TFA:triisopropyl silane:DI water (~50 mg/mL) at room temperature. Cys-PEG-Cys is then purified by precipitating 2× in 1:1 ice cold diethyl ether:n-hexane. TFA is further removed by dissolving the polymer in 0.1 M HCl and removing solvent with rotary evaporation. Cys-PEG-Cys is then obtained after lyophilizing the polymer.

Third Crosslinkable Entity Synthesis: Cys-EDA-Cys

Figure 6:
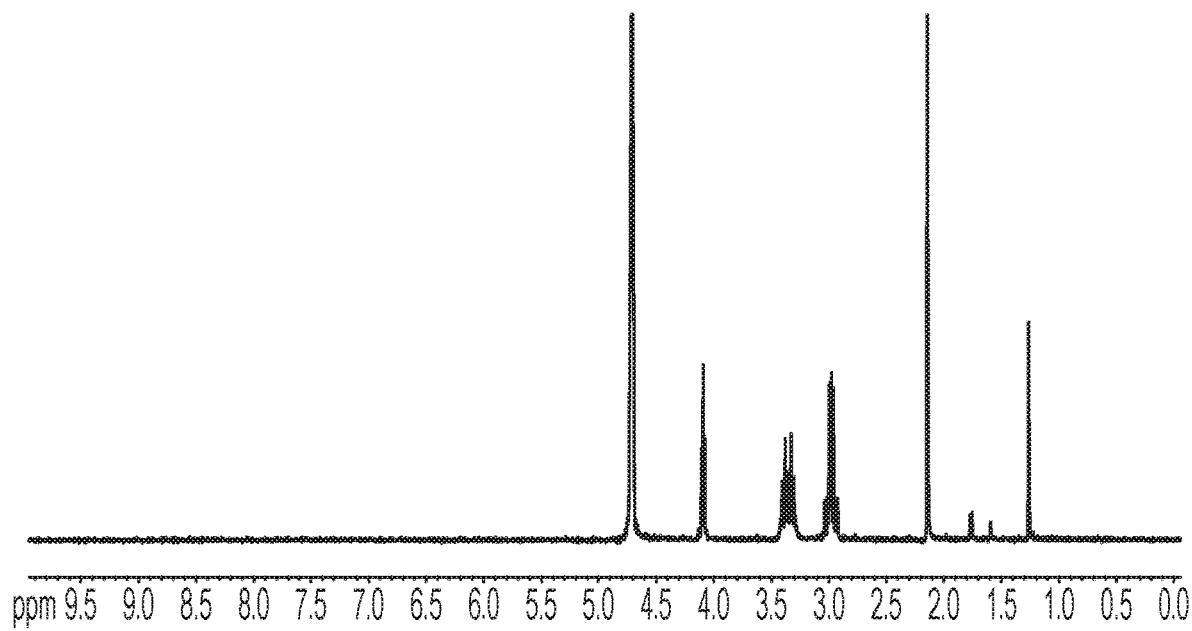
FIG. 6 illustrates $^1$H NMR of Cys-EDA-Cys in deuterated acetone from Example 1.
Figure 7:
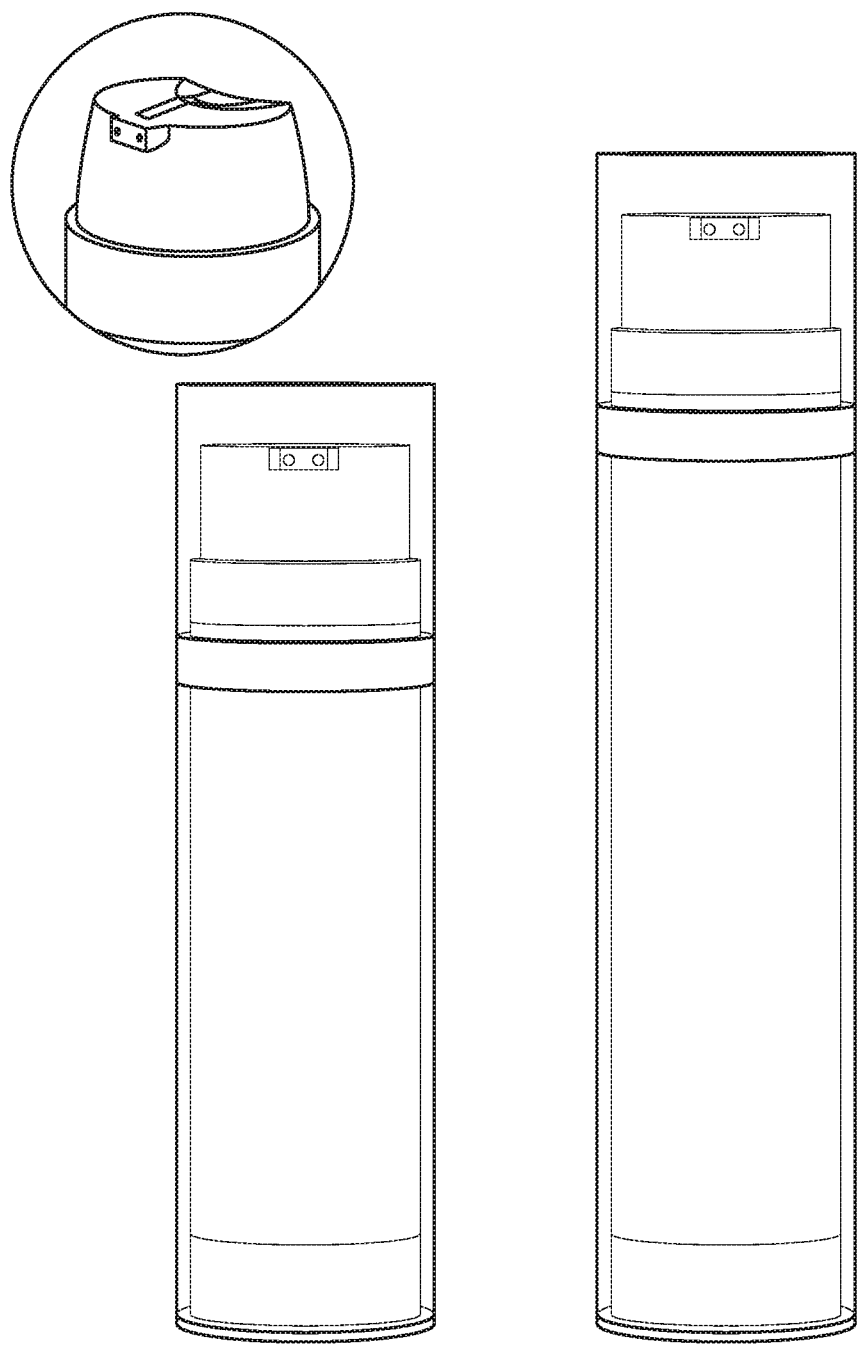
FIG. 7 presents an exemplary packaging of a first and second crosslinkable entity, which are dynamically blended on use. The illustrated packaging shows that the two entities are mixed in a chamber just prior to dispensing
Figure 8:
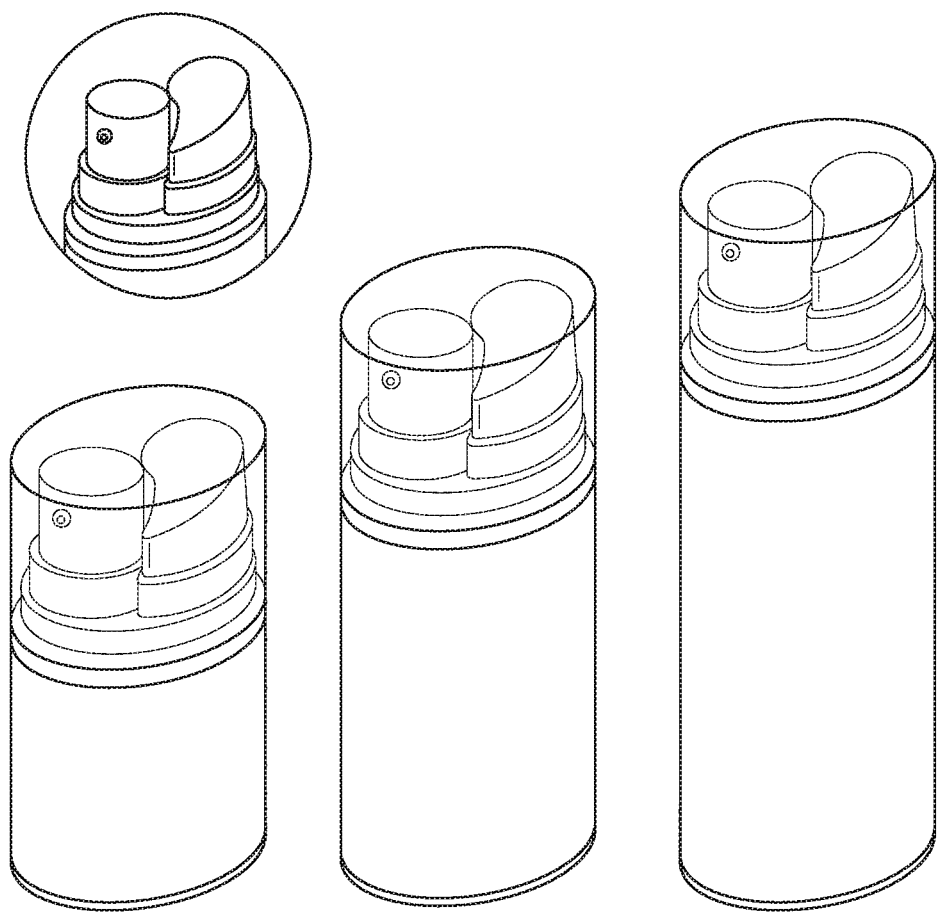
FIG. 8 presents an exemplary packaging of a first and second crosslinkable entity, which can be individually dispensed.

A lower molecular weight Cys-based crosslinkable entity can be prepared using ethylene diamine as the linker (Cys-EDA-Cys). Such a material was prepared in an analogous procedure to the Cys-PEG-Cys described above. A mixture of N-Boc-S-trityl-D-cysteine (2.8 equiv.) and 1,1'-Carbonyldiimidazole (CDI, 2.8 equiv.) in anhydrous DMF (~55 mg N-Boc-S-trityl-D-cysteine/mL) was stirred for 30 minutes at room temperature. EDA was then added directly to the reaction mixture. After reacting for 3.5 h at room temperature, DMF was removed with rotary evaporation and the polymer was extracted into DCM, washing first with water and then brine. The protected product was then isolated with flash chromatography using 1.5:1 ethyl acetate:hexanes containing 0.05% triethylamine. The Boc- and trityl-deprotection was accomplished by adding the polymer to a solution of 0.85:0.10:0.05 TFA:triisopropyl silane:DI water (~50 mg/mL) at room temperature, and stirring for 4 hours. Cys-EDA-Cys was then purified by removing the solvent via rotary evaporation and extracting the product from DCM with DI water (2×). TFA was further removed by dissolving the polymer in 0.1 M HCl and removing solvent with rotary evaporation. Cys-EDA-Cys was then obtained after lyophilizing the polymer. The proton NMR spectrum of Cys-EDA-Cys is depicted in FIG. 6.

Synthesis of Different Variants of Cys Crosslink Moieties

In some embodiments, a second crosslinking entity contains 2 or more aminothiols (i.e., 2 or more aminothiol crosslinkable moieties) each of which may, in at least some embodiments, be conjugated via linker moiety.

In some embodiments, such an aminothiol is a 1,2-, 1,3-, or 1,4-aminothiol or combination thereof. In some embodiments, an aminothiol is D-cysteine, L-cysteine, a derivative of cysteine, or combination thereof. In some embodiments, an aminothiols is capped with another chemical moiety, which for example may be released to expose the aminothiol under physiological conditions.

In some embodiments, a linker may be or comprise a polymer, such as PEG, a diamine or a polypeptide. In some embodiments, a linker may be or comprise a small molecule or amino acid, such as ethylene diamine or lysine.

Example 2. Assessing Characteristics of Crosslinkable Entities, Components and/or Combinations Thereof, and/or of Crosslinked Material(s) they Generate Ex Vivo The present Example describes certain ex vivo strategies that may be used to characterize or assess crosslinkable entities (and/or components and/oror combinations thereof) as described herein, and/or the crosslinked materials formed by their reaction.

Viscosity

In some embodiments, it may be desirable to assess viscosity of preparations of one or both crosslinkable entities separately (e.g., before they have been contacted with one another and/or permitted to crosslink).

Those skilled in the art will be aware of technologies for assessing viscosity. To give but one example, those skilled in the art will be aware of a variety of procedures for viscosity assessment, for example, utilizing a rheometer (e.g., with concentric cylinders, cone & plate, or parallel plate geometry).

As described herein, in some embodiments, preparations of individual crosslinkable moieties for use as described herein may have a viscosity low enough to permit delivery by injection (e.g., via microneedles).

Rheological Properties

Thus, in some embodiments, crosslinkable entities (and/or components and/or combinations thereof) may be assessed for their usefulness as described herein based in whole or in part on one or more rheological properties of the crosslinked material they generate. In some embodiments, one or more rheological properties of a crosslinked material may be adjusted based on polymer moiety and/or crosslink moiety molecular weight (e.g., number average molecular weight), concentration, degree of substitution, as well as on density and/or length of crosslinks within the material, etc.

Those skilled in the art will be familiar with technologies for assessing rheological properties of crosslinked materials as described herein. For example, in some embodiments, rheological assessments may be performed with a rheometer AR-G2. Rheological flow and/or oscillatory analyses may be performed using a Couette geometry (cup diameter=30.42 mm, gap=0.5 mm, and bob diameter and length of 27.95 mm and 42.15 mm, respectively). In some embodiments, it may be desirable to minimize prevent solvent evaporation, for example by thermally isolating (solvent trap) material to be assessed and checking its weight before and after the experiment (difference in weights should desirably be less than 1%). Typically, analyses will be performed under constant temperature (37° C.). In some embodiments, gelation kinetics may be monitored through time sweeping tests, and storage (G') and loss (G") moduli may be measured as function of, for example time at 10 rad/s frequency and 1% stress strain.

In some embodiments, first and second crosslinkable entities may be pre-mixed (e.g., for a short time such as ~5 min), loaded, and measured at the test temperature. Either or both of frequency and flow sweeping tests can be performed after crosslinking between them occurs. In some embodiments, frequency sweeping tests can be conducted isothermally, for example in the frequency range $0.01<\omega<100$ rad/s, while maintaining stress strain, for example at 1%. Normal force can desirably be maintained to a constant value as well. In some embodiments, it will be desirable to take care to ensure that residual stress due to loading is relaxed. In some embodiments, a crosslinked material may be allowed a soak time to equilibrate at the test temperature. In some embodiments, flow sweep experiments can be made isothermally in the shear rate range $0.0005<\gamma<100$ s$^{-1}$ to determine the zero-shear viscosity and/or an intensive shear thinning regime. In some embodiments, data points may be collected once every 100 s.

In some embodiments, a crosslinked material as described herein will desirably have a storage modulus within the range of 50 Pa-10 kPa. In some embodiments, a crosslinked material as described herein will desirably have a storage modulus within the range of 10 Pa-100 Pa. In some embodiments, a crosslinked material as described herein will desirably have a storage modulus within the range of 100 Pa-300 Pa. In some embodiments, a crosslinked material as described herein will desirably have a storage modulus within the range of 300 Pa-1000 Pa. In some embodiments, a crosslinked material as described herein will desirably have a storage modulus within the range of 1 kPa-10 kPa. In some embodiments, a crosslinked material as described herein will desirably have a storage modulus within the range of 5 kPa-10 kPa. In some embodiments, a crosslinked material as described herein will desirably have a storage modulus greater than 10 kPa. Gelation Kinetics In some embodiments, desirable crosslinkable entities interact with one another to generate a crosslinked material with appropriate kinetics as described herein under physiologically relevant conditions (e.g., at 37° C. and/or in the presence of physiologically relevant salts and/or other agents). In some embodiments, it may be useful to assess gelation kinetics in vitro, for example by combining first and second crosslinkable entities together under such physiologically relevant conditions and monitoring their interaction, for example, by assessing dynamic storage modulus (G') and loss modulus (e.g., G"). As will be appreciated by those skilled in the art, the time at which dynamic storage modulus becomes greater than loss modulus, can be considered to be the gelation time.

In some embodiments, the first and second crosslinkable entities are mixed in a vessel (e.g., a test tube); a period of time elapses; the test tube is inverted and the resultant mixture does not flow from the vessel. In some such embodiments, the period of time is 10, 30, 60, 90 or 360 seconds.

In some embodiments, desirable crosslinkable entities (or components/moieties or combinations thereof) are those for which gelation time, determined as described herein when they are combined ex vivo, is less than about 30 minutes.

In some embodiments, an appropriate or desired gelation time will depend on the mode or manner of administration. For example, if the first and second crosslinkable moieties will be combined or otherwise contacted with one another at a site (e.g., within a syringe or at a site of administration) other than the target gelation site, it will typically be desirable that the gelation time be sufficiently long to ensure that significant crosslinking does not occur away from the target gelation site.

Swelling

In some embodiments, crosslinkable entities, components or combinations thereof may be assessed for usefulness in accordance with the present disclosure by determining one or more swelling attributes of the crosslinked material they create. In some embodiments, degree of swelling may be measure based on mass ratio between crosslinked material in a dry form vs a fully swollen form (e.g., that has reached equilibrium with an external aqueous buffer: $Q = M_{swollen}/M_{dry}$). In some embodiments, one or more swelling attributes of a crosslinked material may be adjusted based on polymer moiety and/or crosslink moiety molecular weight (e.g., number average molecular weight), concentration, degree of substitution, as well as on density and/or length of crosslinks within the material, etc. In some embodiments, a crosslinked materials as described herein may have a swelling ratio within the range of 50-1000.

Hyaluronidase Resistance

Those skilled in the art will appreciate that crosslinking can increase the resistance to degradation of biopolymers, resulting in increased durability in situ. To demonstrate this, an HA gel was formed ex vivo and exposed to hyaluronidase, an enzyme naturally present in the body that degrades HA.

HA-gly-CBT (50 µL, 15 mg/mL, PBS) was mixed with either PBS (20 µL) or Cys-PEG-Cys (20 µL, 20 mg/mL) and incubated at 37° C. for 1.5 h. The mixture of HA-gly-CBT and PBS remained a viscous liquid, while the mixture of HA-gly-CBT and Cys-PEG-Cys formed a clear gel. To each formulation was added bovine testes hyaluronidase (5 µL) and the mixtures were vortexed gently to obtain final enzyme concentrations of 100 units/mL. At defined time points, samples were centrifuged to remove insoluble, gel components and an aliquot of each of the supernatants was analyzed. Resistance to degradation was assessed by summing the fraction of remaining soluble HA with a high molecular weight (determined by GPC analysis of the supernatant) with the fraction of remaining insoluble HA (determined by GPC analysis of the supernatant with plate reader).

Figure 9:
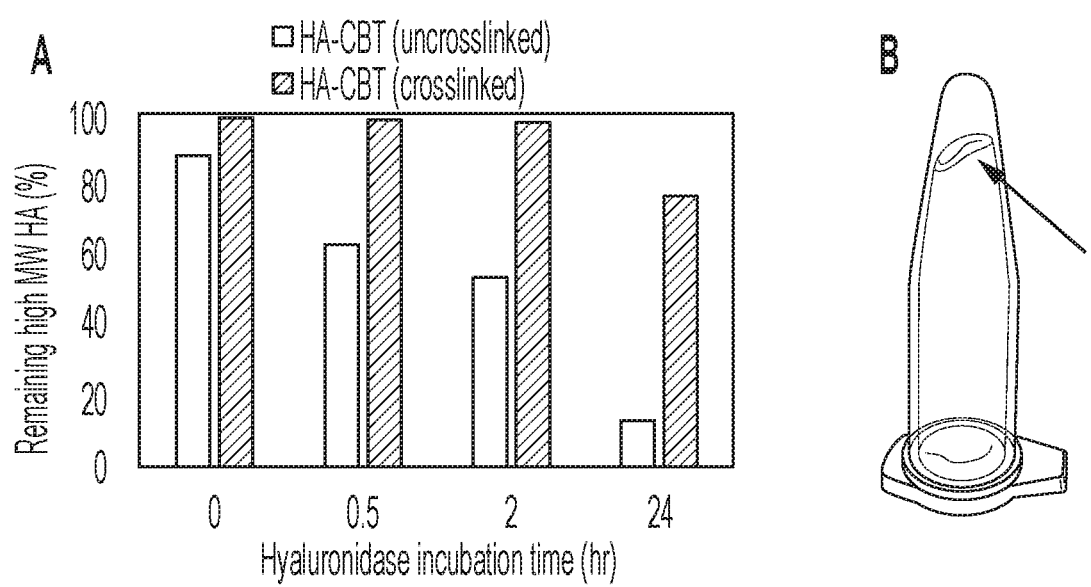
FIG. 9 illustrates resistance to degradation by hyaluronidase of the crosslinked HA-gly-CBT. The plot in FIG. 9A depicts fraction of HA-gly-CBT remaining as an insoluble gel and high molecular weight polymer after incubation with hyaluronidase for both crosslinked and uncrosslinked materials.

Degradation of HA-gly-CBT mixed with PBS was significantly faster than that of the crosslinked HA-gly-CBT (HA-gly-CBT mixed with Cys-PEG-Cys). After 24 h, less than 15% of HA-gly-CBT remained as high molecular weight in the non-crosslinked sample, while >50% of the crosslinked HA-gly-CBT remained as a gel. An image of the gel after 24 h incubation is shown in FIG. 9, and documents the demonstrated resistance to degradation by hyaluronidase.

In some embodiments, the extent of crosslinking in a crosslinked material is sufficient to impart in situ durability. In some such embodiments, the crosslinked material exhibits an increased durability relative to an appropriate reference, such as the corresponding uncrosslinked material.

Example 3: Formulations of a Crosslinkable Entities

The subsections below (i.e. sections 3.1-3.11) provide exemplary formulations, each of which comprise at least one crosslinkable entity. In some embodiments, the component labelled "crosslinkable entity" may be substituted for a different suitable crosslinkable entity as provided herein. In some embodiments, the system comprises a first formulation and a second formulation of sections 3.1-3.11 which are paired together so long as the crosslinkable entity of the first formulation can react with crosslinkable entity of the second formulation to form a crosslinked material.

3.1. Exemplary Serum

A serum (e.g., that may be utilized, for example, as an anti-aging serum), is prepared by combining part A and B as outlined in Table 3.1 and subsequently adding part C until the pH of the serus is about 5.0— about 5.5.

Without wishing to be bound be any particular theory, Applicant notes that exemplary components may, in some embodiments, participate functionally in a serum preparation as suggested below.

TABLE 3.1

| Part | Trade Name | Supplier | INCI/Ingredient Name | % w/w | Function |
|---|---|---|---|---|---|
| A | Water | | Water | Qs to 100.00 | |
| | Dissolvine ® NA2-S | AkzoNobel | Disodium EDTA | 0.15 | Chelate |
| | | Aldrich | Sodium Metabisulfite | 0.05 | Stablizer |

TABLE 3.1-continued

| Part | Trade Name | Supplier | INCI/Ingredient Name | % w/w | Function |
|---|---|---|---|---|---|
| | Structure XL | AkzoNobel | Hydroxypropyl Starch Phosphate | 4.00 | Soothing/sensory feel agent |
| | | | Glycerin | 3.00 | |
| | Recentia ® CS | AkzoNobel | Camellia Sinensis Flower/Leaf/Stem Juice | 0.50 | Soothing plant serum fraction |
| | | | HA-gly-CBT | 0.001-5.00 | Crosslinkable entity |
| | Optiphen Plus | Ashland | Phenoxyethanol, Caprylyl Glycol, Sorbic Acid | qs | Preservative |
| B | | | Citric Acid | 0.23 | pH adjuster |
| | | | Tri-Sodium Citrate Dihydrate | 0.82 | buffer |
| C | | | Citric Acid | qs | |

3.2. Exemplary Lotion

A lotion formulation that may be used as a soothing and/or moisturizing lotion) is prepared as outlined herein Part A is prepared by combining the ingredients summarized in table 3.2 and heating with mixing to 75° C. Separately, part B is prepared by combining the ingredients summarized in table 3.2 and heating with mixing to 75° C. Using high sheer agitation, part B is added to part and mixed at 75° C. The formulation is allowed to cool with moderate mixing. At 35° C., part C is mixed until uniform. pH is adjusted to 5.0±0.5, with the addition of part D.

Without wishing to be bound by any particular theory, Applicant notes that exemplary components may, in some embodiments, participate functionally in a lotion preparation as suggested below.

TABLE 3.2

| Part | Trade Name | Supplier | INCI/Ingredient Name | % w/w | Function |
|---|---|---|---|---|---|
| A | | | Water | qs to 100.00 | Humectant |
| | | | Glycerin | 3.00 | Rheology modifier |
| | | | Xanthan Gum | 0.30 | Preservative |
| | Optiphen Plus | Ashland | Phenoxyethanol, Caprylyl Glycol, Sorbic Acid | qs | Preservative |
| | | | Potassium Sorbate | 0.20 | Humectant |
| B | ARLACEL ™ LC | Croda | Sorbitan Stearate, Sorbityl Laurate | 3.00 | Emulsifier |
| | NATRAGEM E145 | | Polyglyceryl-4 Laurate/Succinate | 2.80 | Emulsifier |
| | | | Stearic Acid | 3.50 | Emulsifier |
| | | | Butyrospermum Parkii (Shea Butter) | 5.00 | Emollient |
| | CRODAMOL ISIS | Croda | Isostearyl Isostearate | 10.00 | Emollient |
| C | | | Water | 30.00 | |
| | | | HA-gly-CBT | 0.001-5.00 | Crosslinkable entity |
| | AQUALANCE | | Water, Erythritol Homarine HCl | 3.00 | Moisturizer |
| D | | | Citric Acid | qs | |

3.3. Exemplary Lotion

A lotion formulation (e.g., that may be used as a natural sun-protecting face lotion) is prepared as outlined herein. Part A is prepared by combining the ingredients summarized in table 3.3 and heating 85° C. Part B is prepared by combining the ingredients summarized in table 3.2 and heating to 85° C. Part C is added to part A with stirring and temperature is maintained. Part B is slowly added to part. A/C with high shear stirring. The mixture is homogenize. The formulation is stirred and cooled to room temperature, adding part D below 40° C.

Without wishing to be bound by any particular theory, Applicant notes that exemplary components may, in some embodiments, participate functionally in a lotion preparation as suggested below.

TABLE 3.3

| Part | Trade Name | Supplier | INCI/Ingredient Name | % w/w | Function |
|---|---|---|---|---|---|
| A | Crodamol ™ GTCC | Croda | Caprylic/Capric Triglyceride | 5.00 | |
| | Crodamol ISIS | Croda | Isostearyl Isostearate | 5.00 | Emollient |
| | Arlacel 1690 | Croda | Sorbitan Isostearate, Polyglyceryl-3 Polyricinoleate | 3.50 | Emollient |
| | Prisorine ™ 3515 | Croda | Isostearyl Alcohol | 2.00 | Emulsifier |
| | Pripure ™ 3759 | Croda | Squalane | 2.00 | Emollient |
| | | | *Butyrospermum Parkii* (Shea) Butter | 1.00 | Emollient |
| B | | | Water | qs | |
| | | | Glycerin | 4.00 | Humectant |
| | | | NaCl | 0.70 | |
| | Optiphen Plus | Ashland | Phenoxyethanol, Caprylyl Glycol, Sorbic Add | qs | Preservative |
| | Keltrol CG-T | Kelco | Xanthan Gum | 0.1 | Stabilizer |
| C | Solaveil XT-300 | Croda | Titanium Dioxide, Caprylic/Capric Triglyceride, Polhydroxystearic Acid, Stearic Acid, Alumina | 24.00 | Inorganic broadspectrum sunscreen |
| | | | Water | 20.00 | |
| D | Fruitliquid Blueberry EC | Croda | Water, Glycerin, *Vaccinium Myrtillus* Fruit Extact | 2.00 | Antioxidant & Protection |
| | | | HA-gly-CBT | 0.001-5.00 | Crosslinkable entity |

3.4. Exemplary W/O Emulsion

An emulsion formulation (e.g., that may be used as a soothing w/o cream) is prepared as outlined herein Part A is prepared by mixing until dissolved the ingredients summarized in table 3.4. The ingredients from Part B are then added to Part A with high shear to afford the formulation.

Without wishing to be bound by any particular theory, Applicant notes that exemplary components may, in some embodiments, participate functionally in an emulsion preparation as suggested below.

TABLE 3.4

| Part | Trade Name | Supplier | INCI/Ingredient Name | % w/w | Function |
|---|---|---|---|---|---|
| A | | | Water | Qs to 100.00 | |
| | | | Sodium Chloride | 1.00 | Salt |
| | | | Potassium Sorbate | 0.30 | Preservative |
| | | | Sodium Benzoate | 0.30 | Preservative |
| | | | Lactic Acid | 0.05 | pH adjustment |
| | | | HA-gly-CBT | 0.001-5.00 | Crosslinkable entity |
| B | Crodamol ™ GTCC | Croda | Caprylic/Capric Triglyceride | 9.00 | Emollient |

TABLE 3.4-continued

| Part | Trade Name | Supplier | INCI/Ingredient Name | % w/w | Function |
|---|---|---|---|---|---|
| | Solaveil ™ XT-300 | Croda | Titanium Dioxide, Caprylic/Capric Triglyceride, Polyhydroxystearic Acid, Stearic Acid (and) Alumina | 5.00 | Sunscreen |
| | SP Arlacel ™ 1690 MBAL | Croda | Sorbitan Isostearate (and) Polyglyceryl-3 Polyricinoleate | 3.00 | W/O emulsifier |
| | Pripure ™ 3759 | Croda | Squalane | 3.00 | Emollient |
| | Crodamol ™ ISIS | Croda | Isostearyl Isostearate | 2.00 | Emollient |
| | Span™ 80 | Croda | Sorbitan Oleate | 1.00 | Co-emulsifier |
| | | | Tocopherol (and) *Helianthus Annuus* (Sunflower) Seed Oil | 0.20 | Antioxidant |

3.5. Exemplary Hydrogel Mask

An hydrogel mask formulation (e.g., that may be used as a solid fiber mask with impregnated serum) is prepared as outlined herein. Part: A is prepared by dissolving Tetrasodium EDTA in water under propeller mixing. Gum are pre-dispersed in glycerin to make slurry. The slurry is added to the Tetrasodium EDTA solution under propeller mixing, mixing until uniform and lump-free. Part A is heated to 85-90° C. to hydrate the gums. While Part A is hot, pan B as summarized in Table 3.5 is added with mixing.

Part C ingredients as summarized in Table 3.5 are pre-mixed and added to parts A and B. The hot solution is immediately poured in molds and allowed to set undisturbed. Once the gel is cooled and is set, the formulation is packed suitably.

Without wishing to be bound by any particular theory, Applicant notes that exemplary components may, in some embodiments, participate functionally in a hydrogel mask preparation as suggested below.

TABLE 3.5

| Part | Trade Name | Supplier | INCI/Ingredient Name | % w/w | Function |
|---|---|---|---|---|---|
| A | | | Water | qs | |
| | | | *Aloe barbadensis* Leaf Juice | 5.00 | |
| | | | TetraSodium EDTA | 0.10 | Soothing |
| | | Kelco | Carrageenan | 0.80 | Chealating Agent |
| | | Kelco | Locust Bean Gum | 0.60 | Gelling Agent |
| | | | Glycerin | 14.00 | Gelling Agenl |
| | | | HA-gly-CBT | 0.001-5.00 | Crosslinkable entity |
| | | | Tocopherol | 0.05 | Cosmetic Active Antioxidant |
| B | | | NaCl | 0.80 | Stabilizer |
| | | | Water | 3.20 | |
| C | Optiphen Plus | Ashland | Phenoxyethanol, Caprylyl Glycol, Sorbic Acid | qs | Preservative |

3.6. Exemplary Powder to Cream Serum

A serum formulation (e.g., that may be used as a BB (Beauty Balm) Powder to Cream Soothing Serum) is prepared as outlined herein. Procedure: Add all ingredients of part A as summarized in table 3.6 and mix with high shear until a homogeneous mixture is obtained. Add part B as summarized in table 3.6 powder ingredients and mix until free flowing powder is obtained.

Without wishing to be bound by any particular theory, Applicant notes that exemplary components may, in some embodiments, participate functionally in a serum preparation as suggested below.

TABLE 3.6

| Part | Trade Name | Supplier | INCI/Ingredient Name | % w/w | Function |
|---|---|---|---|---|---|
| A | Water | | Water | Qs 100.00 | |
| | | | Glycerin | 30% | Humectant |
| | | | Hyaluronic Acid-CBT Polymer | 0.001-5.00 | Crosslinkable entity |
| | TEGOSOFT ® TN | Evonik | C12-C15 alkyl benzoate | 2.00 | Emollient |
| | | | *Butyrospermum parkii* (shea butter) | 2.00 | Emollient |
| | | | tocopherol | | Antioxidant |
| | Optiphen Plus | Ashland | Phenoxyethanol, Caprylyl Glycol, Sorbic Acid | qs | Preservative |
| B | AEROSIL ® R 812 S | | Silica silylate | 10.0 | Stabilizer |
| | SIPERNAT ® 11 PC | | Hydrated silica | 1.00 | Sensory modifier |
| | | | Pigment | qs | optional |

3.7. Exemplary Solid Formulation

A solid formulation (e.g., that may be used as a targeted deep wrinkle solid stick) is prepared as outlined herein. Procedure: Heat part A as described in table 3.7 to 95° C. and mix until dissolved, then add to Phase B as described in table 3.7 heated to 95° C., cool to 75° C. and add phase C. Mix to uniform and pour into molds or containers.

Solidification point 70° C.

Appearance: Bright amber transparent to translucent gel

Without wishing to be bound by any particular theory, Applicant notes that exemplary components may, in some embodiments, participate functionally in a solid preparation as suggested below.

TABLE 3.7

| Part | Trade Name | Supplier | INCI Name | % w/w | Function |
|---|---|---|---|---|---|
| A | AJK OD 2046* | Ajinomoto NA | Octyl Dodecanol, Dibutyl Lauroyl Glutamide, Dibutyl Ethylhexanoyl Glutamide | qs 100.00 | Gelling mixture |
| B | Floramac Macadamia oil | Floratech | *Macadamia Integrifolia* Seed Oil | 20.00 | Natural emollient |
| | Florasun 90 | Floratech | *Helianthus Annus* (Sunflower) Seed Oil | 23.65 | Natural emollient/ Moisturization |
| | Evening Primrose oil | Hallstar | *Oenothera Biennis* (Evening Primrose) oil | 5.00 | Natural emollient |
| | Sensolene | Hallstar | Ethylhexyl Olivate | 5.00 | Light emollient |
| | ELDEW SL-205 | Ajinomoto NA | Isopropyl Lauroyl Sarcosinate | 5.00 | Light emollient |
| | Schercemol DISM Ester | Lubrizol | Diisostearyl Malate | 5.00 | Stability improvement |
| | Schercemol DISD | Lubrizol | Diisostearyl Dimer Dilinoleate | 5.00 | Stability improvement |
| | Schercemol 185 | Lubrizol | Isostearyl Neopentanoate | 5.00 | Emollient |
| | Liponate NEB | Lipo Chemicals | C12-15 Alkyl Benzoate | 5.00 | Clarity enhancement, |
| | ELDEW PS-306 | Ajinomoto NA | Phytosteryl/Behenyl Octyldodecyl Lauroyl Glutamate | 1.00 | Gel stability |
| | Oryza Tocotrienol | Oryza Oil & Fat Co | *Oryza Sativa* (rice) Bran Oil (and) Tocotrienols (and) Tocopherol | 0.30 | Natural antioxidant |
| | Astaxanthin-5C | Oryza Oil & Fat Co | Caprylic/Capric Triglyceride, *Haematococcus Pluvialis* Extract, Astaxanthin, Tocopherol | 0.05 | Anti-oxidant |
| C | | | HA-gly-CBT | 0.001-5.00 | Crosslinkable entity |

3.8. Exemplary Mist

A mist formulation (e.g. that may be used as a revitalizing mist with pH 5 antioxidant) is prepared as outlined herein. The ingredients as summarized in Table 3.8 are combined to afford part A. C The ingredients as summarized in Table 3.8 are combined to afford part B. Part. A is added to part B while mixing until uniform. Part C is added to the mixture of parts A and B. The resultant mixture is mixed until uniform. The pH is adjusted to pH to 4.0-5.0 for stability. The formulation is packaged in a spray bottle.

TABLE 3.8

| Part | Trade Name | Supplier | INCI/Ingredient Name | % w/w | Function |
|---|---|---|---|---|---|
| A | Water | | Water | qs to 100.00 | |
| | | | Glycerin | 6.00 | |
| B | ProdhyFluid ® | Prod'Hyg | Sorbiatn Oleate, Polysorbate 80, Caprylic/Capric Triglyceride, Squalane, *Prunus Amygdalus* Dulcis Oil, Polysorbate 20, Tocopherol | 5.00 | Emulsifier |
| | | | Tocopherol | 0.20 | |
| | PhytoTrace Rice | Inolex | *Oryza Sativa* (Rice) Seed Extract/ Glycerin/Water | 1.00 | Soothing skin feel |
| | PhytoTrace Fig | Inolex | *Ficus Carica* (Fig) Fruit Extract/ Glycerin/Water | 1.00 | Soothing skin feel |
| | Grapefruit Floral Water | | *Citrus Grandis* (Grapefruit) Flower Water | 0.50 | Energizing |
| | Roman Chamomille Water | | *Anthemis Nobilis* (Roman Chamomille) Water | 0.50 | Energizing |
| | Optiphen Plus | Ashland | Phenoxyethanol, Captylyl glycol, Sorbic acid | qs | Preservative |
| | | | Glutathione | 0.20 | Stablizer |
| C | | | Cys-PEG-Cys | 0.001-5.00 | Crosslinkable entity |
| D | | | Citric Acid | qs to pH 4-5 | Stabilizer |

3.2 Exemplary Serum

The ingredients of part A as summarized in Table 3.9 are combined and mixed until uniform. The ingredients of part B as summarized in Table 3.9 are combined and added to part A, mixing until homogeneous. Part C is added. Part D is added until the pH is adjusted to 5.0-5.5 with 25% Citric Acid Solution as needed.

Without wishing to be bound by any particular theory, Applicant notes that exemplary components may, in some embodiments, participate functionally in a serum preparation as suggested below.

TABLE 3.9

| Part | Trade Name | Supplier | INCI/Ingredient Name | % w/w | Function |
|---|---|---|---|---|---|
| A | Water | | Water | Qs 100.00 | |
| | Dissolvine ® NA2-S | AkzoNobel | Disodium EDTA | 0.15 | Chelate |
| | | Aldrich | Sodium Metabisulfite | 0.05 | |
| | Structure XL | AkzoNobel | Hydroxypropyl Starch Phosphate | 4.00 | Soothing |
| | | | Glycerin | 3.00 | |
| | Recentia ® CS | AkzoNobel | *Camellia Sinensis* Flower/Leaf/Stem Juice | 0.50 | plant serum fraction |
| | Optiphen Plus | Ashland | Phenoxyethanol, Caprylyl Glycol, Sorbic Acid | qs | Preservative |

TABLE 3.9-continued

| Part | Trade Name | Supplier | INCI/Ingredient Name | % w/w | Function |
|---|---|---|---|---|---|
| B | | | Citric Acid | 0.23 | |
| | | | Tri-Sodium Citrate Dihydrate | 0.82 | |
| C | | | Water | 50.00 | |
| | | | HA-Cys | 0.001-5.00 | Crosslinkable entity |
| D | | | Citric Acid | qs | |

3.10. Exemplary Powder

A powder formulation (e.g., that may be used as a powder to cream formulation with inhibitors to slow prevent cross linking in product and until within skin) is prepared as outlined herein. The ingredients of part A as summarized in Table 3.10 are combined and mixed with high shear until a homogeneous mixture is obtained. Part B powder ingredients are added and mixed until free flowing powder is obtained, Part C is folded in and mixed until uniform.

Without wishing to be bound by any particular theory, Applicant notes that exemplary components may, in some embodiments, participate functionally in a serum preparation as suggested below.

TABLE 3.10

| Part | Trade Name | Supplier | INCI/Ingredient Name | % w/w | Function |
|---|---|---|---|---|---|
| A | Water | | Water | Qs 100.00 | |
| | | | Glycerin | 30% | Humectant |
| | | | Cys-PEG-Cys | 0.001-5.00 | Linker |
| | | | Glutathione | 0.20 | Antioxidant |
| | | | Tocopherol | 0.20 | Antioxidant |
| | TEGOSOFT ® TN | Evonik | C12-C15 alkyl benzoate | 2.00 | Emollient |
| | | | *Butyrospermum parkii* (shea butter) | 2.00 | Emollient |
| | Optiphen Plus | Ashland | Phenoxyethanol, Caprylyl Glycol Sorbic Acid | qs | Preservative |
| B | AEROSIL ® R 812 S | | Silica silylate | 10.0 | Stabilizer |
| | SIPERNAT ® 11 PC | | Hydrated silica | 1.00 | Sensory modifier |
| | | | Pigment | 1.00 | Skin Color, Radiance modifier |
| C | | | Hyaluronic Acid-CBT | 0.001-5.00 | Crosslinkable entity |

3.11 Exemplary Lotion

A lotion (e.g., that may be used as a liquid crystal solid nanoparticie dual action lotion is prepared as outlined herein. The components in part A as summarized in table 3.11 are mixed, and heated to 50° C. The components of part B are added, and the mixture is heated to 65° C.-70° C. The components of Phase C as summarized in table 3.11 are mixed at room temperature. The heated components of parts A and B are then mixed together in a vessel under lamellar flow conditions, which create a lyotropic liquid-crystalline mixed phase (AB) with a mean particle size of 150 nm. The lyotropic liquid-crystalline mixed parts A and B are then mixed with part C to form a dispersion. Once uniform, Phase D is added, pH adjusted through the addition of Phase E, with gentle mixing, then cooled to room temperature.

Without wishing to be bound by any particular theory, Applicant notes that exemplary components may, in some embodiments, participate functionally in a serum preparation as suggested below.

TABLE 3.11

| Part | Trade Name | Supplier | INCI/Ingredient Name | % w/w | Function |
|---|---|---|---|---|---|
| A | Water | | Water | 3.00 | |
| | | | Cys-PEG-Cys | 0.001-5.00 | Linker |
| | | Tri-K | Sodium Lauroyl Lactylate | 0.50 | Emulsifier |
| | | Kelco | Xanthan Gum | 0.10 | Thickening agent |
| | | | Glutathione | 0.10 | Antioxidant |
| B | | | Cetyl Palmitate | 20.00 | Emulsifier |
| | Biobase S | Tri-K | Glyceryl Stearate, Sodium Stearoyl Lactylate, Cetearyl Alcohol | 0.50 | Emulsifier |
| C | | | Water | qs to 100.00.00 | |
| D | | | Water | 40.00 | |
| | | | HA-gly-CBT | 0.10-5.00 | Crosslinkable entity |
| | | | Preservative | qs | Preservative |
| E | | | Citric Acid | qs pH 4-5 | |

Example 4: Assessing Characteristics of Crosslinkable Entities, Components or Combinations Thereof, and/or of Crosslinked Materials they Generate in Porcine Skin The present Example describes use of porcine skin studies to characterize or assess crosslinkable entities (and/or components and/or combinations thereof) as described herein, and/or the crosslinked materials formed by their reaction.

In some embodiments, a system comprising first and second crosslinkable entities is applied to porcine skin. In some such embodiments, application of the first crosslinkable entity is separated in time (i.e., by a period of time) from application of the second crosslinkable entity. In some embodiments, multiple different separating periods of time may be assessed. A person of skill in the an will appreciate that the period of time may be dependent on desired depth of penetration, skin type and target location. In some such embodiments, multiple different separating periods of time as a function of desired dept of penetration skin type and target location may be assessed.

In some embodiments, degree of penetration of the first and/or second crosslinkable entities into the porcine skin is assessed at one or more time points after administration of one or both of the crosslinkable entities. For example, in some embodiments, such assessment(s) may be made at one or more time points selected from the group consisting of 1, 4, 12, 24 and 48 hours.

In some embodiments, one or more porcine skin samples may be thawed, for example at room temperature (e.g., for 30 min or more) prior to use. In some embodiments, hair may be clipped from such samples (e.g., using scissors), and samples may be rinsed, e.g., using 0.9% saline solution.

In some embodiments, subcutaneous in situ gelation may be assessed by administering first and second crosslinkable entities to a site or sites on or in the sample. For example, in some embodiments, solutions of first and second crosslinkable entities may be injected (e.g., separately or as a mixture, optionally after a premix period, and optionally at one or more different concentration ratios) into the sample. Alternatively or additionally, in some embodiments, porcine skin samples may be excised until their underlying dermis layer is reached, and first and second crosslinkable moieties can be administered to fill the void.

In some embodiments, skin samples to which first and second crosslinkable moieties have been administered may be maintained under stable conditions (e.g., stored at room temperature in a Petri Dish) for a period of time to permit crosslinking (e.g., gelation) to occur in situ.

In some embodiments, degree of crosslinking may be assessed at one or more time points after administration (e.g., after injection of a mixture or of the first or, more likely, the second, crosslinkable moiety), for example by sectioning the sample(s) (e.g., using a scalpel). In some embodiments, such sectioning involves preparing small (e.g., about 0.4 cm×0.4 cm) squares, which can be frozen (e.g., by immersion in a isopentane/dry ice bath) and stored, for example at −80° C.

Whether or not such storage has occurred, thin (e.g., about 20 µm) skin sections can be obtained (e.g., using a cryostat), and can be imaged (e.g., using a confocal microscope).

Porcine Skin Penetration of HA-gly-CBT

Frozen, porcine skin was equilibrated to room temperature, and cut into ~1.5×1.5 cm squares. Prior to incubation, one skin sample was tape stripped twenty times to remove the stratum corneum (SC). All skin pieces were washed with PBS and then placed into Franz diffusion cells (1 cm$^2$) at 37° C. for 5 min. PBS or HA-gly-CBT (~250 kDa, 10 mg/mL, PBS) (150 µL) were applied in the donor compartments, the donor compartments sealed with parafilm, and the cells incubated in a humidified oven at 37° C. for 18 h.

The skin surface was washed three times in the Franz cell with PBS, and then a small region in the center of the application area was excised with a surgical scalpel. The skin tissue was placed into OCT in a biopsy mold and snap frozen by placing the mold into a methylpentane/dry ice slurry. The frozen skin was sectioned on a cryostat microtome into 20 µm sections. A drop of ProLong Gold was placed on each section, and covered with a coverslip prior to imaging. Fluorescent images were taken with a 10× objective on a ZeissAxioPlan2 using a DAPI filter (Zeiss filter 49) to visualize the location of HA-gly-CBT.

Figure 10:
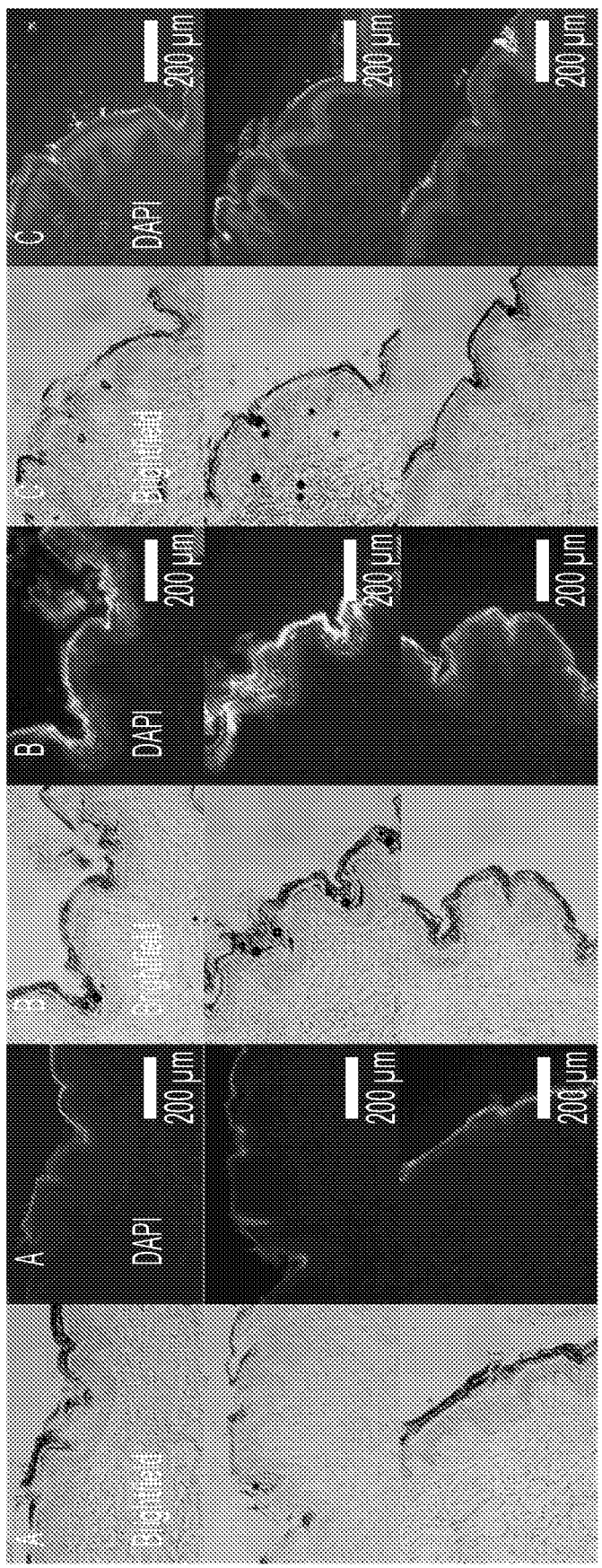
FIG. 10 illustrates bright field and fluorescent (DAPI filter) images of porcine skin sections after topical application of PBS (A) and HA-gly-CBT (B) to intact porcine skin and HA-gly-CBT (C) to tape stripped porcine skin.

Compared to the skin treated with only PBS, the skin treated with HA-gly-CBT exhibited significantly more fluorescence in the epidermis, indicative of skin penetration of the HA-gly-CBT past the SC (FIG. 10). A stronger fluorescence was observed in the skin which was tape stripped prior to topical application of HA-gly-CBT, indicating an increase in penetration after the top barrier of the skin is disrupted.

Verification of penetration of intact HA-gly-CBT was assessed using gel permeation chromatography (GPC). HA-gly-CBT (15 mg/mL, 300 µL, DI water containing 0.5% Tween$_{20}$) was applied topically to 6 separate, porcine skin pieces in Franz diffusion cells. The samples were incubated for 18 h at 37° C. in the sealed donor compartment and the skin surfaces washed three times with PBS. The stratum corneum was isolated from the samples using tape strips, then the epidermis was scraped off the dermis, and the dermis cut into small pieces. HA-gly-CBT was extracted from each of the skin sections (top 8 layers of SC, bottom 8 layers of SC, epidermis, and dermis) by incubation in 1:1 PBS:methanol at 37° C. overnight. The volume of the extracts was reduced with rotary evaporation, and the concentrated solutions analyzed by GPC (using the same conditions as described in Example 1, mobile phase of 9:1 DI:MeOH, 0.2 M $NaNO_3$).

Figure 11:
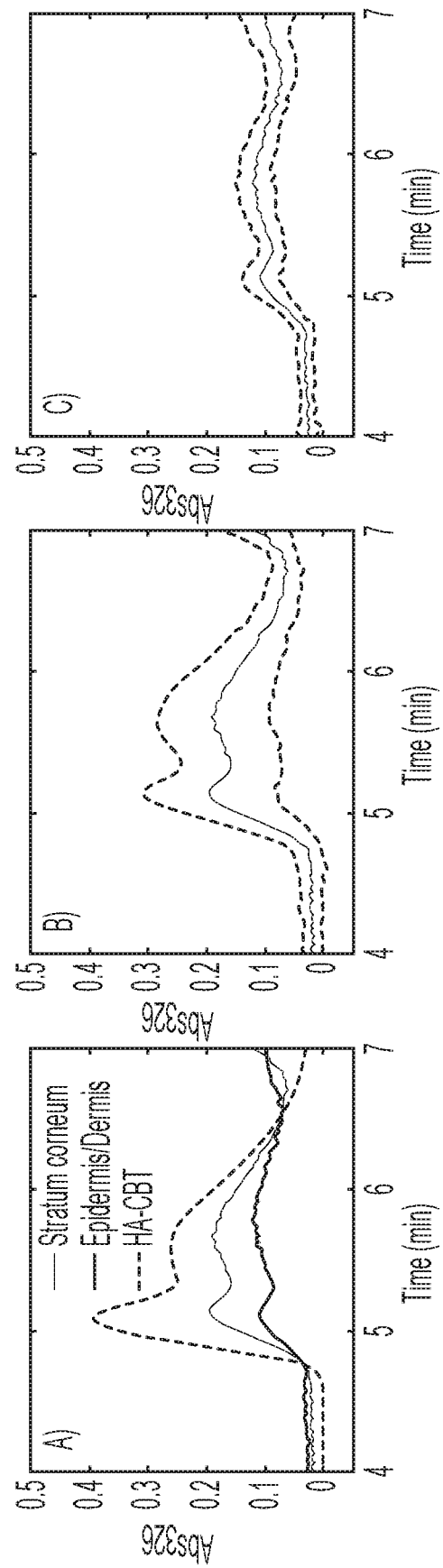
FIG. 11 illustrates GPC analyses of skin extracts after topical application of HA-gly-CBT.

The GPC signal from each layer (stratum corneum, epidermis, dermis) of the samples was averaged across all 6 samples (FIG. 11). In both the stratum corneum and epidermis/dermis extracts, there was a signal corresponding to HA-gly-CBT was observed, indicating the delivery of intact HA-gly-CBT to those respective layers of the skin. Error bars for the SC and epidermis/dermis extracts are included in FIGS. 11b and 11c, respectively, to demonstrate reproducibility of the results.

In Situ Crosslinking in Porcine Skin

To assess the biocompatibility of the cross linking reaction between the two crosslinkable entities, the two components were introduced directly into porcine skin. HA-gly-CBT (30 μL, 5 mg/mL, PBS) was injected into two porcine skin samples with a 31-gauge insulin syringe right below the skin surface. Cys-PEG-Cys (20 mg/mL, PBS) was then injected (using the same technique) into one of the skin samples 1 h after the HA-gly-CBT injection. Both skin samples were incubated at 37° C. overnight in a humidified oven. Following incubation, the samples were frozen and sectioned, as described above.

Figure 12:
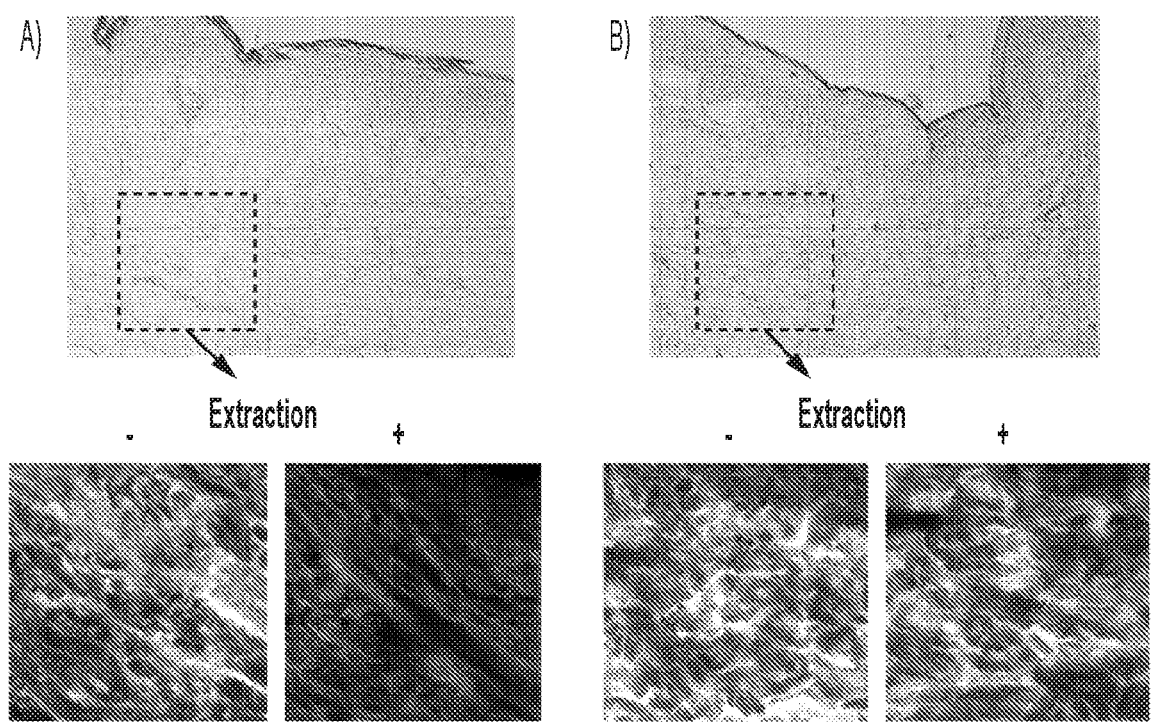
FIG. 12 illustrates bright field and fluorescent (DAPI filter) images of porcine skin sections after injection of HA-gly-CBT (A) or HA-gly-CBT followed by Cys-PEG-Cys (B). Sections were imaged both directly after sectioning and after washing to extract soluble HA-gly-CBT.

Half of the sections from each group were washed in DI water at 37° C. for 1.5 hour to remove free HA-gly-CBT. The slides were imaged using a fluorescent microscope as described above. The dermal fluorescence intensity in the washed sections of the skin injected with HA-gly-CBT alone was significantly reduced compared to the unwashed sections (FIG. 12A). However, the skin samples that were injected with both crosslinkable entities exhibited similar dermal fluorescence intensity in both washed and unwashed sections (FIG. 12B). These results suggest that the two crosslinkable entities reacted within the skin to form an insoluble gel that was not removed during the slide washing step.

Example 5. Administration to Humans

The present Example describes administration of a system as described herein to a human, and assessment of one or more skin characteristics in light of such administration.

As described herein, first and second crosslinkable entities are administered to a skin site. In some embodiments, both crosslinkable entities are administered to the same site; in some embodiments, each may be administered to a different site so long as both ultimately arrive at a target site of interest, so that a crosslinked material, formed by reaction of the first and second crosslinkable entities, is formed or otherwise provided in situ at the target site.

In some embodiments, one or both of the first and second crosslinkable entities is administered to the target site (e.g., by injection). In some embodiments, one or both of the first and second crosslinkable entities is administered to a site above (i.e., external) to the target site, so that the crosslinkable entity(ies) must penetrate skin tissue in order to arrive at the target site. Among other things, the present disclosure provides crosslinkable entities having particular characteristics (e.g., lipophilicity and/or molecular weight (e.g., number average molecular weight), etc) that facilitate such penetration.

In some embodiments, administration of the first crosslinkable entity is separated in time (i.e., by a period of time) from that of the second crosslinkable entity. In some such embodiments, the period of time is sufficient to permit substantial penetration of the first-administered crosslinkable entity toward and/or into the target site prior to administration of the second-administered crosslinkable entity.

In some embodiments, multiple administrations are performed for at least one of the cross-linkable entities; in some embodiments, multiple administrations are performed for each of the cross-linkable entities. In some embodiments, administration of both crosslinkable moieties is considered a "dose" of a provided system. In some embodiments, administration of one crosslinkable entity to a subject who has previously received administration of the other crosslinkable entity is considered a "dose" of a provided system. In some embodiments, multiple doses are administered.

In some embodiments, a crosslinkable entity is a formulation of Example 3. In some embodiments the formulation of the first crosslinkable entity and the formulation of the second crosslinkable entity are the same. In some embodiments the formulation of the first cross linkable entity and the formulation of the second crosslinkable entity are different.

Assessing Skin Improvement

In some embodiments, one or more characteristics of skin (e.g., skin at and/or above the target site) is assessed after the system has been administered (e.g., at one or more time points selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, and 31 days or more after the administration—for example after administration of any particular dose or of a complete dosing regimen). In some embodiments, one or more characteristics of skin (e.g., skin at and/or above the target site) is assessed after the system has been administered (e.g., at one or more time points selected from the group consisting of 1, 2, 3, 4, 5, 6, 7, 8, 9, 10, 11 and 12 months or more after the administration—for example after administration of any particular dose or of a complete dosing regimen). In some embodiments, one or more characteristics of skin (e.g., skin at and/or above the target site) is assessed about 3.5 days after the system has been administered. In some embodiments, one or more characteristics of skin (e.g., skin at and/or above the target site) is assessed about 9 days after the system has been administered.

For example, in some embodiments, one or more visual features of skin is assessed after system administration (e.g., as compared with prior to such administration). In some embodiments, visual features are assessed by one or more expert graders with reference to the Global Aesthetic Improvement Scale (GAIS) which, as is known in the art, is a validated, standardized 5-point scale for measurement of response to cosmetic procedures, which has been shown to have good intra- and inter-rater reliability, and intra-class correlation coefficients generally in the range of 0.85-0.95 (see, for example, Carruthers & Carruthers, *J. Cosmet Laser Therp.* 12:235, 2010) In some embodiments, administration of a system as describe herein achieves at least a 1-grade improvement in GAIS scale.

Alternatively or additionally, in some embodiments, one or more skin features may be assessed with an established scale such as, for example, the Lemperle wrinkle scale, a Subject Satisfaction scale (typically 7-point), the Allergan skin roughness scale, or any other appropriate scale. In some embodiments, any validated scale that includes subjective and/or objective assessment of one or more physical, functional, or visual attributes (e.g., smoothness, radiance, firmness, elasticity, volume, etc) of skin may be utilized.

In some embodiments, one or more skin features may be or relate to enhanced mechanical support of dermal extracellular matrix, fibroblast elongation and/or spreading, up-regulation of type II TGF-beta receptor or downstream targets thereof (e.g., type I collagen synthesis), up-regulation of connective tissue growth factor, and/or combinations thereof (see, for example, Quan et al., *J Invest Dermatol.* 133:658, 2013). Those skilled in the art are aware of strategies for assessing such features, including after injection into human skin (including damaged, e.g., photodamaged, human skin) (see, for example, Wang et al *Arch Dermotal.* 143:155. 2-7).

In some embodiments, skin hydration may be assessed after administration of a provided system. In some such embodiments, skin hydration is measured, for example with a corneometer (e.g., a corneometer CM825, which provides a conductance measure of the relative moisture content within skin). In some embodiments, administration of a system as described herein achieves a statistically significant improvement in skin hydration; in some such embodiments, such improvement is at least 10%, 15%, 20%, 25% or more, for example when measured at a time that is 12, 24, 36 or 48 hours after administration as described herein. For example, when the crosslinked material (HA-gly-CBT+Cys-PEG-Cys) was administered to samples, a 26% improvement in skin hydration was observed immediately following application of the material. Additionally, long lasting skin hydration on clean undamaged skin was observed, in excess of 72 hrs (as assessed with the Courage+Khazaka Corneometer® CM825).

A 20 mg/ml HA-gly-CBT solution was prepared in deionized water, polysorbate 20 & glycerin. A second solution of Cys-PEG-Cys in PBS (20 mg/mL) was prepared and the pH adjusted to 5.5-6.5 with NaOH. The HA-gly-CBT solution (20 µl) and a solution of the commercial HA benchmark serum (20 µl) were applied to 3 cm×3 cm areas on the volar forearm immediately following baseline readings. Additional Corneometer readings were measured at 0.5 and 6 hours. After 6 hours, the Cys-PEG-Cys solution (20 µl) was applied to the HA-gly-CBT test site and a phosphate buffer solution (20 µl) was applied to the commercial HA benchmark serum site. Additional Corneometer readings were then measured at 12 hr, 24 hr, 48 hr, 72 hr and 96 hr. The results are tabulated in Table 3.12.

The benchmark commercial HA (Hyaluronic Acid) serum was a blend of high and low molecular weight hyaluronic acids, with 1.5% pure hyaluronic acid, described by the manufacturer as capable of replenishing moisture to produce plumped, youthful, supple skin. The ingredient list for the commercial HA Serum benchmark includes water, glycerin, hydroxyethylpiperazine ethane sulfonic acid, sodium hyaluronate, PEG-60 hydrogenated castor oil, *cereale* seed extract/rye seed extract, calcium pantothenate, dipeptide diaminobutyroyl benzylamide diacetate, ascorbyl glucoside, disodium EDTA, pentylene glycol, phenoxyethanol, and chlorphenesin.

TABLE 3.12

| Time (Hrs) | HA-gly-CBT/Cys-PEG-Cys | | Commercial HA Serum | |
| --- | --- | --- | --- | --- |
|  | % change to baseline | Std Dev | % change to baseline | Std Dev |
| Baseline | 0 | — | 0 | — |
| 0.5 | 26% | +/−2.9 | 17% | +/−2.2 |
| 6 | 20% | +/−4.9 | 6% | +/−4.1 |
| 12 | 21% | +/−6.0 | 13% | +/−4.0 |
| 24 | 14% | +/−9.0 | 5% | +/−3.9 |
| 48 | 14% | +/−4.2 | 0% | +/−4.2 |
| 72 | 6% | +/−4.0 | −5% | +/−3.8 |
| 96 | 5% | +/−4.9 | −5% | +/−2.9 |

Figure 13:
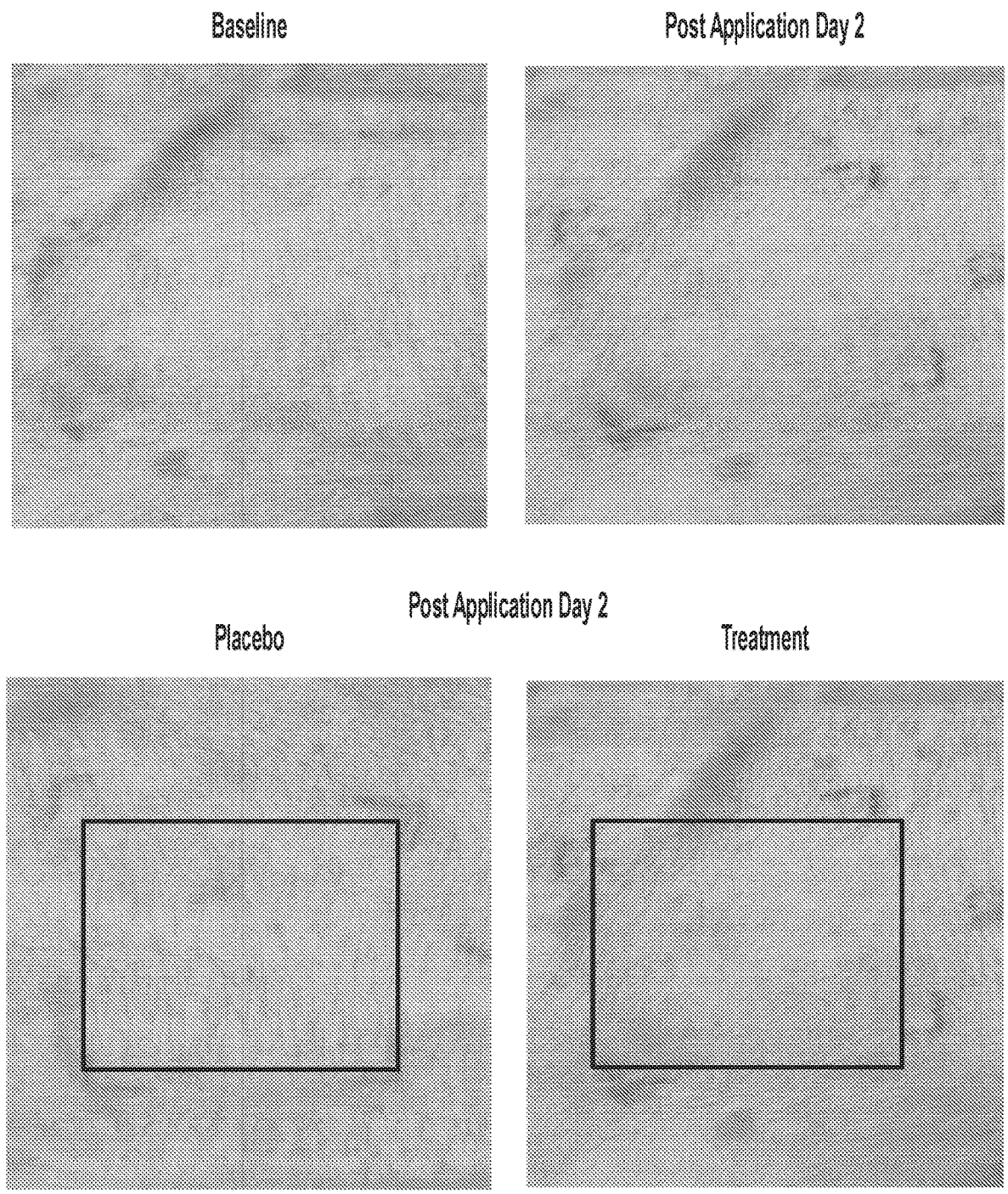
FIG. 13 presents photographs of skin two days after application of the provided system, as compared to the baseline and application of a placebo, illustrating improvement in skin smoothness.

In some embodiments, skin smoothness may be assessed after administration of a provided system. In some such embodiments, skin smoothness is measured, for example, by 3D skin profilometry, for example using a Canfield Promos device and/or by silicon/epoxy cast scanning. In some embodiments, administration of a system as described herein achieves a statistically significant increase in skin smoothness, and/or increasing smoothness over time (with or without additional administrations). For example, visual improvement to skin smoothness after administration of the provided system was demonstrated using a 7-point skin smoothness improvement scale. Two days after application of the system, a two-grade improvement was noted as depicted in FIG. 13.

In some embodiments, skin thickness may be assessed after administration of a provided system. In some such embodiments, skin thickness may be assessed, for example by ultrasound profiling (see, for example, Van Mulder et al. *Vaccine* 35:1810, 2017). In some embodiments, administration of a system as described herein achieves a statistically significant increase in skin thickness.

In some embodiments, relevant skin may have been damaged (e.g., due to a disease, disorder, or condition, or to a surgical, cosmetic, or dermatological treatment), and improvements to such damaged skin are assessed. In some embodiments, damaged skin may be or comprise laser (e.g., fractional laser) treated skin, intense-pulse-light-treated skin, microneedled skin, skin subjected to chemical peel treatment, skin exposed to dermabrasion, traumatically injured skin (including by surgery), skin suffering from a medical condition such as skin atrophy, extreme dryness, etc.

Alternatively or additionally, in some embodiments, relevant skin may be skin that is wrinkled or otherwise shows signs of aging, or may be skin with respect to which additional plumpness and/or resilience is desired.

In some particular embodiments, skin of interest may be or comprise skin at a site selected from the group consisting of full face and/or specific targets of a subject's face such as lips, lower lip, upper lip, tear troughs or other sites around the eyes (e.g., crow's feet), nasolabial folds, forehead, cheeks back of hands, ear lobes, knees, neck, décolletage, arms, legs, torso, buttocks feet, and combinations thereof, including, for example, full face, etc.

Assessing Penetration

In some embodiments, it may be desirable to assess penetration of one or both crosslinkable entities administered to a human as described herein.

In some embodiments, a biopsy is obtained of a site to which a provided system has been administered or delivered, and histology on the biopsy is performed to assess degree (e.g., amount) and/or depth of penetration. In some embodiments, crosslinkable entity(ies) and/or crosslinked material is detected in the epidermis, dermis or underlying hypodermis or below. In some embodiments, an amount of crosslinkable entity(ies) is detected within the skin in the biopsy (e.g., on, at, in, or below the epidermis, dermis or underlying hypodermis and/or otherwise at the target site) that is a meaningful (e.g., at least 5%, 10%, 15%, 20%, 25%, 30%, 35%, 40%, 45%, 50%, 55%, 60%, 65%, 70%, 75%, 80%, 85%, 90%, 95% or more) percentage of that administered (e.g., to a surface of the skin and/or to a site external to the target site).

HA-Gly-CBT Penetration into Disrupted Human Skin

Figure 14:
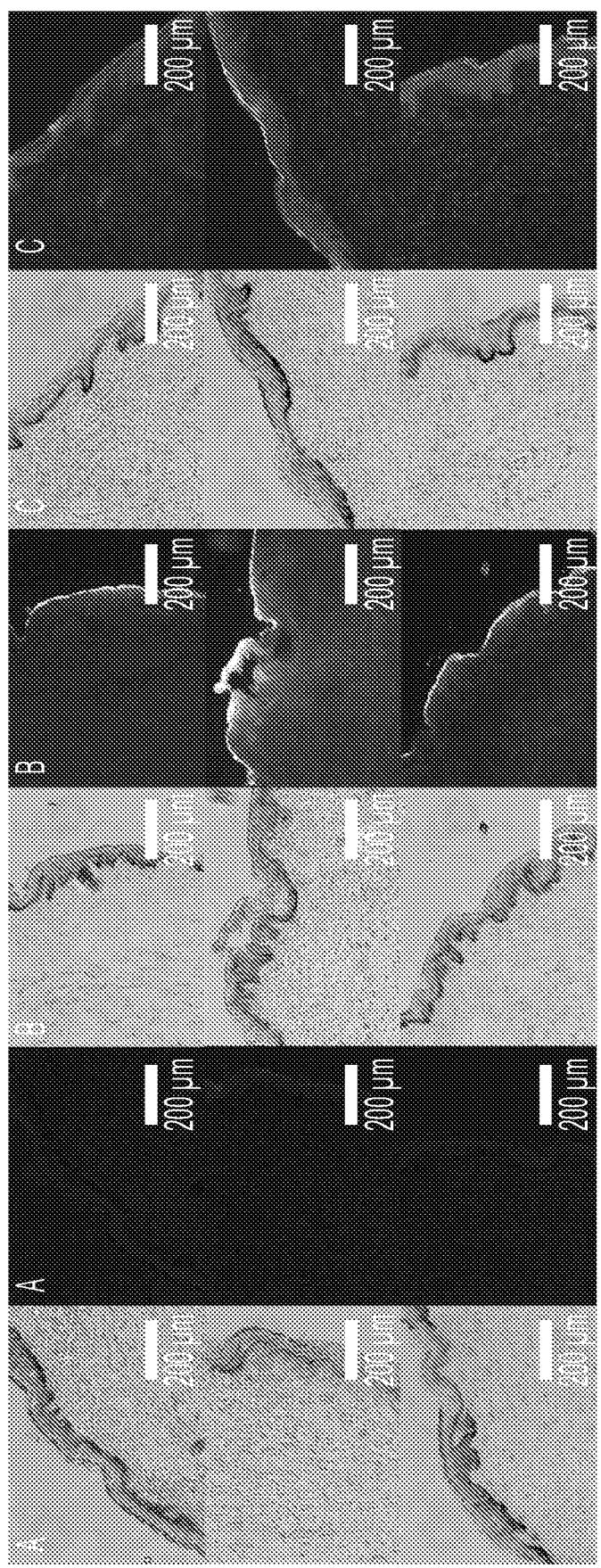
FIG. 14 illustrates bright field and fluorescent (Cy5 filter) images of human skin sections after topical application of PBS (A) and HA-gly-CBT tagged with AlexaFluor 647 (B and C) to disrupted human skin. Skin was tape stripped prior to application in one sample (B) and treated with a dermaroller containing 500 μm needles in another (C).

In some embodiments, the penetration of the crosslinking entity into human skin can be increased through skin barrier disruption techniques. For example, the ex vivo penetration of HA-gly-CBT (tagged with AlexaFluor 647 hydrazide) into human skin, which was pretreated with different techniques was assessed with microscopy. Prior to application of the material, one skin sample was tape stripped twenty-five times to remove the majority of the stratum corneum. In a second sample, HA-gly-CBT was applied to the surface of the skin, and the skin was then treated with a dermaroller (500 μm needle), rolling over the product 40 times. Both samples were incubated in Franz cells in a humidified oven at 37° C. for 20 h after topical application. The samples were sectioned to 20 μm and imaged on a fluorescent microscope using a Cy5 filter, as described above (FIG. 14).

A significant fluorescent signal was observed in the human epidermis and dermis of the skin, which was tape stripped prior to topical application of HA-gly-CBT. In the sample treated with HA-gly-CBT and the dermaroller, a significant fluorescent signal was observed in the epidermis, but only a feint signal was observed in the dermis. Both examples illustrate how disrupting the barrier of human skin can facilitate penetration of HA-gly-CBT deep into human skin.

Figure 18:
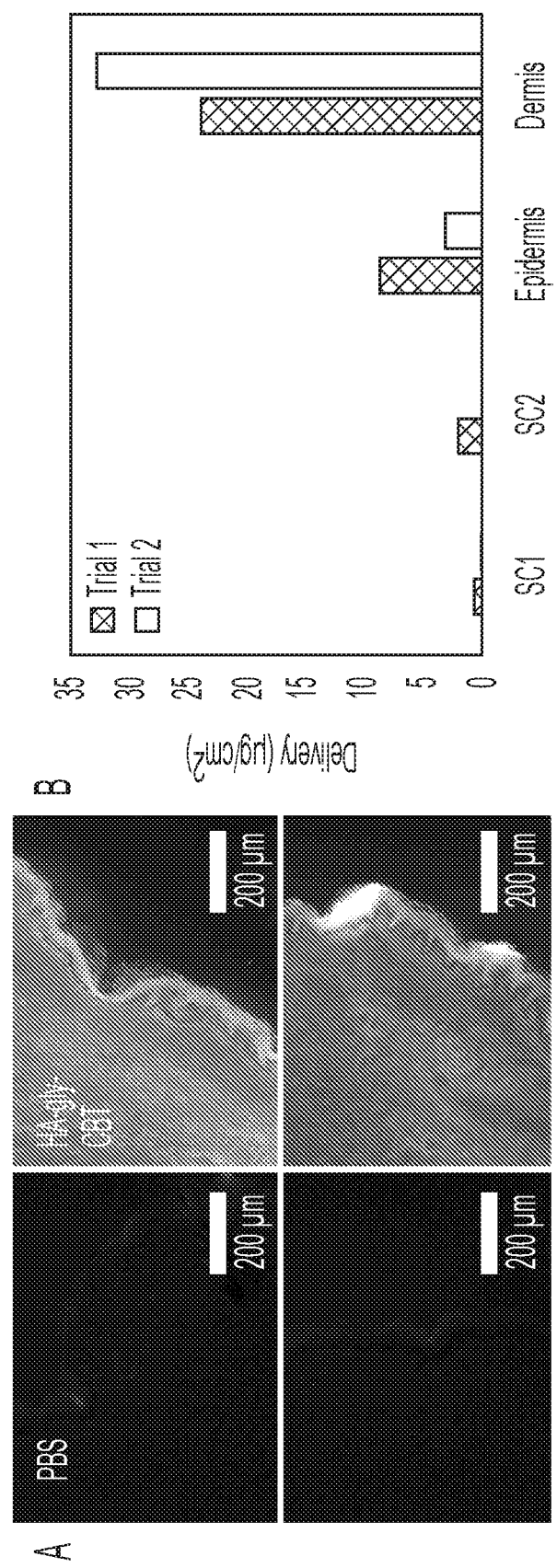
FIG. 18 illustrates topical delivery of HA-gly-CBT (50 kDa, tagged with IR dye) into human skin treated with a dermaroller containing 500 μm needles.

The ability of dermarolling to facilitate topical penetration of HA-gly-CBT was further probed via application of a 50 kDa variant of HA-gly-CBT. HA-gly-CBT (50 kDa, tagged with AlexaFluor 647 hydrazide) was applied topically to human skin, rolled twenty times with a dermaroller (500 μm needles). The skin was transferred to a Franz cell and incubated at 37° C. for 20 h. The skin was frozen, sectioned, and imaged on a fluorescent microscope with a Cy5 filter to observe depth of penetration. (FIG. 18A). Two additional human skin samples were treated similarly. The stratum corneum was removed from the samples with tape stripping (20×) and the epidermis and dermis isolated with a scalpel. After extracting HA-gly-CBT (overnight at 37° C.) from each skin layer into 1:1 PBS:Methanol, the concentration of HA-gly-CBT was quantified by measuring the fluorescence of the AlexaFluor dye in each extract on a plate reader (FIG. 18 B).

A significant amount of HA-gly-CBT (50 kDa) was detected in both the epidermis and dermis after treatment with a dermaroller. Observed permeation of HA-gly-CBT suggests feasibility of topical delivery of a stable, HA-based crosslinked material deep into the dermis when coupled with subsequent, concurrent, or previous topical delivery of a cysteine-based crosslinkable entity.

Example 6: Exemplary Systems

Figure 15:
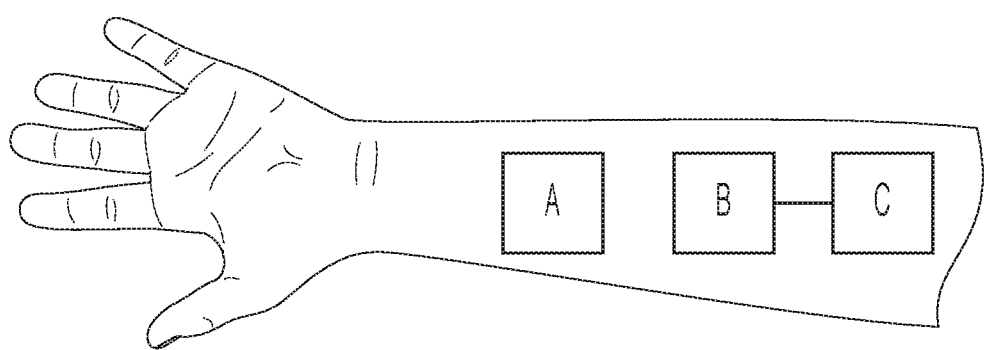
FIG. 15 presents the exemplary sites of administration from Example 6.

Sites of administration on the skin of the left volar forearm (see FIG. 15) of the subject were prepared for administration of the crosslinkable entites. The sites were prepared by cleaning with mild soap and tepid water for 30 seconds, rinsing the sites for an additional 30 under tepid water and patting the sites dry. Semi-transparent Scotch Tape was repeatedly applied to each site and removed until each of the sites glistened slightly (about 40 cycles).

A first formulation was administered to each of the sites:

| Site of Administration | First Formulation |
| --- | --- |
| A | PBS |
| B | 2% HA-gly-CBT in PBS |
| C | 2% HA-gly-CBT in PBS |

Upon administration of the first composition, each site was covered with about 3 cm³ of Tegaderm™ type film. A period of 2 hours was allowed to elapse. The Tegaderm™ paper was removed. The sites were allowed to equilibrate for 10 minutes. Visual appearance of sites were photographed under both visible light and ultraviolet light (~365 nm).

A second crosslinkable formulation were administered to each of the sites:

| Site of Administration | Second Formulation |
| --- | --- |
| A | 2% CYS-PEG-CYS in PBS |
| B | PBS |
| C | 2% CYS-PEG-CYS in PBS |

Upon administration of the second composition, each site was covered with about 3 cm³ of Tegaderm™ type film. The sites were left covered overnight. The Tegaderm™ paper was removed. The sites were allowed to equilibrate for 10 minutes. At which time, the sites of administration were examined using visible and ultraviolet (365 nm) light. Recordable fluorescent signal was not observed at sites A and B. Fluorescent signal was clearly visible at the site C (see FIG. 15) indicating crosslinked material had penetrated the skin.

The sites of administration were washed at least once per day using mild soap and water and patted dry. The sites of administration were kept dry at all other times.

Figure 16:
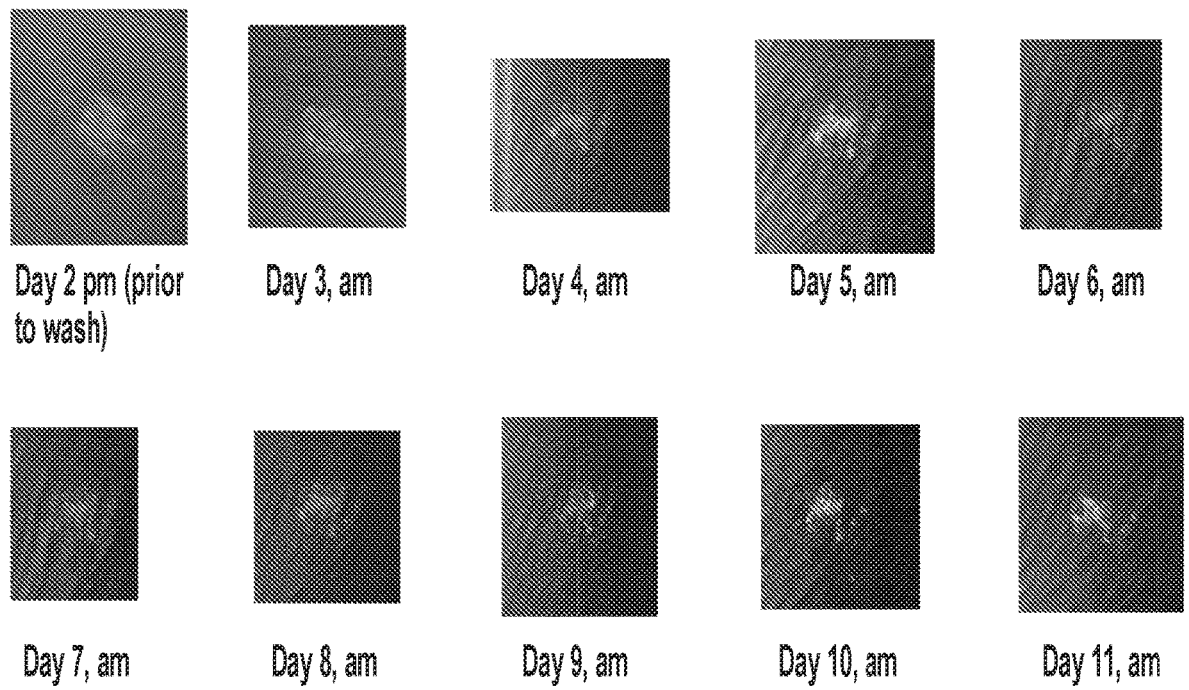
FIG. 16 presents images at time points post administration of the system as described in Example 6.

Visual appearance of sites were photographed under both visible light and ultraviolet light (~365 nm) daily. Recordable fluorescent signal was not observed at sites A and B. Fluorescent signal was clearly visible at site C indicating crosslinked material had penetrated skin and was still present (FIG. 16).

11 days post administration of the system, the sites were examined again using ultraviolet light. Fluorescent signal was clearly visible at site C indicating crosslinked material had penetrated skin and was still present after 11 days. Additionally, the subjects exhibited no evidence of any tolerability issues. The site of administration had an improved skin texture 11 days post administration as compared to the site prior to administration of the system.

Example 7: Histological Measurement

The left volar forearm was administered with the following crosslinkable entities in a 3 by 3 cm square:
1. 75 μL of 2% HA-gly-CBT,
2. 2 hours of time elapsed
3. 75 μL of 2% Cys-PEG-Cys,
4. 3 hours of time elapsed
5. 75 μL of 2% HA-gly-CBT
6. 2 hours of time elapsed
7. 75 μL of 2% Cys-PEG-Cys Tegaderm™ was applied on top of the application site between and after each administration of a crosslinkable entity. The administration process was repeated daily for 2 days, for a total of 4 administrations of both HA-gly-CBT and Cys-PEG-Cys. On the third morning, a 4 mm biopsy was taken in the center of the application square, after washing and sterilizing the site. The biopsy was immediately frozen in OCT.

Figure 17:
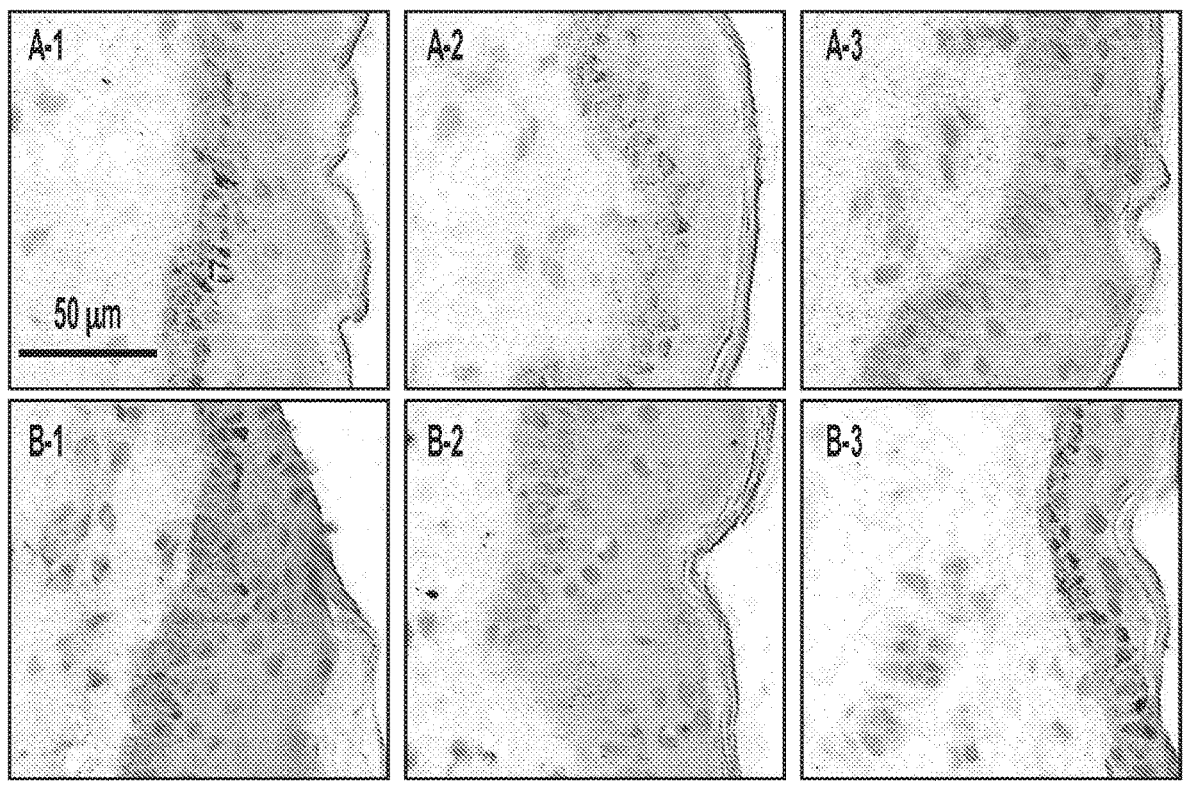
FIG. 17 presents images of biopsies post administration of the system as described in Example 7.

The biopsy was sectioned with a cryostat, and the sections fixed in neutral buffered formalin on the slides. The slides were then stained with Alcian Blue to detect hyaluronic acid and Nuclear Fast Red as a counter stain (FIG. 17). Some slides were also pretreated with hyaluronidase prior to staining, to remove hyaluronic acid. As seen in FIG. 17, there is a strong signal in the epidermis and upper part of the dermis for slides which were not pretreated with hyaluronidase.

The invention claimed is:

1. A method of improving a skin attribute, wherein the method comprises forming a composition at a site below the stratum corneum, wherein the composition comprises a first crosslinkable entity comprising a hyaluronic acid (HA) polymer conjugated to a first crosslink moiety via a linker, wherein the first crosslink moiety is a cyanobenzothiazole (CBT) crosslink moiety and the linker is glycine, wherein the method further comprises topical administration of the first crosslinkable entity to a skin site, which topical administration is carried out prior to, simultaneously, or after topical administration to the skin site of a second crosslinkable entity, wherein the second crosslinkable entity comprises at least one cysteine second crosslink moiety conjugated to a polymer, wherein the skin site is abraded before, after, or simultaneously with the topical administration of one or both of the first and second crosslinkable entities.

2. The method according to claim 1, wherein the polymers of the first and second crosslinkable entities are the same.

3. The method according to claim 1, wherein the polymer of the second crosslinkable entity is selected from the group consisting of PEG, PEG-diamine, polyacrylic acid, N-(2-Hydroxypropyl) methacrylamide (HPMA), polycaprolactone (PCL), and poly (lactic-co-glycolic acid) (PLGA).

4. The method according to claim 1, wherein the at least one cysteine second crosslink moiety is independently selected from the group consisting of D-cysteine, and L-cysteine.

5. The method according to claim 1, wherein the polymer of the second crosslinkable entity is, or comprises, a diamine, optionally wherein the diamine is ethylene diamine.

6. The method according to claim 1, wherein the second crosslinkable entity is Cys-EDA-Cys.

7. The method according to claim 1, wherein the skin attribute is selected from the group consisting of thickness, aesthetics, moisture content, smoothness, wrinkles, radiance, firmness, elasticity, atrophic skin, scars, fine line wrinkles, and skin translucency.

8. The method according to claim 1, wherein the administration of the first and second crosslinkable entities is carried out simultaneously, optionally wherein the first and second crosslinkable entities are combined prior to administration, or as they are administered.

9. The method according to claim 1, wherein the first and second crosslinkable entities are administered repeatedly.

10. The method according to claim 1, wherein the skin site is abraded in that it is treated is by tape stripping, fraction laser treatment, or microneedling.

11. The method according to claim 10, wherein the skin site is treated by microneedling.

12. The method according to claim 1, wherein the skin site is abraded after the topical administration of one or both of the first and second crosslinkable entities.

13. The method according to claim 11, wherein the microneedling is performed after the topical administration of one or both of the first and second crosslinkable entities.

* * * * *